(12) United States Patent　　(10) Patent No.: US 9,756,297 B1
Clements　　(45) Date of Patent: Sep. 5, 2017

(54) CAMERA FOR VIEWING AND SENSING THE HEALTH OF A USER SITTING ON A TOILET

(71) Applicant: Sigmund Lindsay Clements, Montreal (CA)

(72) Inventor: Sigmund Lindsay Clements, Montreal (CA)

( * ) Notice: Subject to any disclaimer, the term of this patent is extended or adjusted under 35 U.S.C. 154(b) by 253 days.

(21) Appl. No.: 14/791,895

(22) Filed: Jul. 6, 2015

(51) Int. Cl.
　　*H04N 7/18*　　(2006.01)
　　*A61B 5/00*　　(2006.01)
　　*A61B 5/021*　　(2006.01)
　　*A61B 5/01*　　(2006.01)
　　*E03D 9/08*　　(2006.01)
　　*H04N 5/232*　　(2006.01)
　　*H04N 5/225*　　(2006.01)
　　*G06K 9/00*　　(2006.01)
　　(Continued)

(52) U.S. Cl.
　　CPC .............. *H04N 7/185* (2013.01); *A61B 3/14* (2013.01); *A61B 5/0008* (2013.01); *A61B 5/0077* (2013.01); *A61B 5/01* (2013.01); *A61B 5/021* (2013.01); *A61B 5/082* (2013.01); *A61B 5/444* (2013.01); *A61B 5/6891* (2013.01); *A61B 5/742* (2013.01); *E03D 9/08* (2013.01); *G06K 9/00771* (2013.01); *H04N 5/2256* (2013.01); *H04N 5/23203* (2013.01); *H04N 5/23219* (2013.01); *G06T 2207/30088* (2013.01); *G06T 2207/30096* (2013.01)

(58) Field of Classification Search
　　CPC .... H04N 5/1857; A61B 5/0077; A61B 5/444; A61B 5/445; G06T 7/0012; G06T 2207/30004; G06T 2207/30088; G06T 2207/30096
　　See application file for complete search history.

(56) References Cited

U.S. PATENT DOCUMENTS 6,238,337 B1 * 5/2001 Kambhatla .......... A61B 5/0002
　　　　　　　　　　　　　　　　　　　　　　　　　600/300
7,689,016 B2 * 3/2010 Stoecker ............... G06F 19/321
　　　　　　　　　　　　　　　　　　　　　　　　　382/128

(Continued)

FOREIGN PATENT DOCUMENTS

CN　　　104846991 A * 9/2015
DE　　　EP 2138640 A1 * 12/2009 ............... E03D 9/08

(Continued)

*Primary Examiner* — John Villecco

(57) ABSTRACT

A cameras is connected to a device to move the camera over the user's body, posterior, and back, stationary cameras can also be used. The camera's view of the user, is show on a display, and allows a user to view difficult to view areas of their body, while they are sitting on a toilet. Some viewed areas might be neglected by being difficult to view. Being able to view the body areas lets the user, and or a computer, visually diagnosis the areas, for possible health concerns. Health sensors can also be used to perform health tests on the user's body. Health tests can include skin cancer, and blood pressure, etc. Heath test data is displayed, and can be sent to health providers, over the internet, for diagnosis. By practicing preventative health, problems can be detected early, allowing for early medical attention and management of possible health problems.

6 Claims, 25 Drawing Sheets

(51) Int. Cl.
*A61B 5/08* (2006.01)
*A61B 3/14* (2006.01)

(56) References Cited

U.S. PATENT DOCUMENTS

| | | | | |
|---|---|---|---|---|
| 8,194,952 | B2 * | 6/2012 | Mertz | A61B 5/444 |
| | | | | 382/128 |
| 8,213,695 | B2 * | 7/2012 | Zouridakis | A61B 5/0059 |
| | | | | 382/128 |
| 8,543,519 | B2 * | 9/2013 | Guyon | G06F 19/345 |
| | | | | 706/12 |
| 9,212,477 | B2 * | 12/2015 | Tiagai | G06T 1/0014 |
| 9,383,914 | B2 * | 7/2016 | Clements | G06F 3/013 |
| 9,427,187 | B2 * | 8/2016 | Gilbert | A61B 5/0059 |
| 9,477,317 | B1 * | 10/2016 | Clements | G06F 3/017 |
| 9,594,500 | B2 * | 3/2017 | Clements | G06F 3/013 |
| 2012/0114202 | A1 * | 5/2012 | Manson | G06T 7/33 |
| | | | | 382/128 |
| 2013/0245458 | A1 * | 9/2013 | Spector | A61B 1/00009 |
| | | | | 600/476 |
| 2015/0000025 | A1 | 1/2015 | Clements | |
| 2015/0000026 | A1 | 1/2015 | Clements | |
| 2015/0059076 | A1 | 3/2015 | Tiagai | |
| 2016/0100789 | A1 * | 4/2016 | Huang | G06T 7/0012 |
| | | | | 600/306 |

FOREIGN PATENT DOCUMENTS

| | | | |
|---|---|---|---|
| JP | 10176362 A | * | 6/1998 |
| JP | 2003052669 A | * | 2/2003 |
| JP | 2006061296 A | * | 3/2006 |
| JP | 2006183417 A | * | 7/2006 |
| JP | 2007332750 A | * | 12/2007 |
| JP | 2008002137 A | * | 1/2008 |
| JP | 2008202282 A | * | 9/2008 |
| JP | 2009270951 A | * | 11/2009 |
| KR | 2013048471 A | * | 5/2013 |

* cited by examiner

CAMERA FOR VIEWING AND SENSING THE HEALTH OF A USER SITTING ON A TOILET

CROSS REFERENCE TO RELATED APPLICATIONS

This application claims the benefit of provisional patent application Ser. Nos. 62/044,414 filed 2 Sep. 2014, 62/033,634 filed 5 Aug. 2014, 62/021,110 filed 5 Jul. 2014, and 62/081,579 19 Nov. 2014.

This application claims the benefit of patent application Ser. No. 14/556,144 filed 29, Nov. 2014, and Ser. No. 14/312,697 filed 24, Jun. 2014.

SEQUENCE LISTING

None

BACKGROUND FIELD OF THE EMBODIMENT

This application relates to cameras viewing a user while they sit on a toilet, allowing the user to view, hard to view areas of their body, on a display. The application relates to using the camera's view of the body, and or health sensors to measure or diagnosis the user's health. The application relates to the user using the camera's view of the elimination positions to direct a bidets water stream to their elimination positions.

BACKGROUND OF THE EMBODIMENTS

Users have used mirrors, for self-examination of their posteriors, genitals, and back. Using a mirror for examination of the user's posteriors and back can be awkward, and difficult. The user holding a mirror steady in a location, between their legs, for an extended period of time may be strenuous. In may be difficult to position a light, to adequately illuminate the posterior and back positions.

The mirror flips the order of things in the direction perpendicular to its surface. Users can perceive their bodies mirrored images as being flipped. It may be difficult for the user to analyse a perceived flipped image of their body.

It is difficult for a user to view their back. A user may need to position their back, so that the back is viewable in the mirror, and look over their shoulder to see the reflection in the mirror. Using a mirrored view to move their hand to a location on their back is difficult due to having to move in a reversed direction. Two mirrors can be used one to view the back, the second to view the first mirrors view, though this can be inconvenient to arrange.

Back scratchers have been used to scratch an itchy part of a person's back, because it's difficult for the user to touch parts of their back with their fingers. The use of back scratchers demonstrates the difficulty in a person has accessing, or viewing and touching their back.

A user could use a video camera, smart phone camera, or computer camera connected to a video monitor to image their posterior, and back. The user may have to hold the camera steady, and direct its viewing angle. In the case of the computer camera, the computer's location, might not be a comfortable setting for self-examination.

Drawbacks of a Camera Inside a Toilet Bowel

Jung Yeong Mo's, Bidet and method for controlling same, WO2012086924 A2, filling date Nov. 10, 2011 uses a camera which is attached to a bidet cleaning wand, the camera is connected to a computer, and the computer is connected to a video monitor. The monitor is used to view, a user's elimination positions while they are sitting on a toilet, to visually discern possible health problems with the user's elimination positions, and posterior, that may need attention, and to view the effectiveness of the bidet's cleaning of the user. A video camera connected to video monitor, has been used to view a user's elimination positions, while the elimination positions are being sprayed with water. The view allow the user to view, how well their elimination positions are being cleaned A drawback of Jung Yeong Mo's, camera bidet is it only views the user's elimination positions and doesn't view the whole posterior, or whole body of the user. The bidet water stream isn't directed by a computer. The user's health isn't checked by a computer. Only the user's visual inspection is used to detect health ailments.

A problem with the view is the camera uses computer zooming to enlarge the view of the elimination position, computer zoomed images become pixelated and lose viewing definition.

The camera's angles of the view of the elimination positions doesn't change when the angle of the body area being viewed changes. The camera view doesn't remain perpendicular to a viewed area, which can create perspective distortion. Perspective distortion is a warping or transformation of a viewed area that differs significantly from what the object would look like with a normal focal length.

The user has to touch buttons to operate the camera, which may have bacteria and viruses on them. The bacteria on the buttons may be transferred to the user's fingers when touched.

Other Body Viewing Devices

Full body scanning and viewing, use cameras and laser's, such as those made by the Human Solutions and TC company, to 3D image a user's body, and are only used to measure the user size, and changes in the user's size, for body weight changes, and body muscle changes, Some body scanners are used to fit clothes for the user's body.

An example of remote viewing of a user's body is the use of robots for surgery. A health care provider can control a Da Vinci robot surgeon, while viewing a 3D image of the body on a screen. A robot made by the Anvari Company, called Zeus, is used to operate remotely on a patient.

The electronic bidets cameras and body viewing cameras, known suffer from a number of disadvantages:

Disadvantages (a) A camera doesn't look at the whole posterior, and other areas of the user's body, such as, the back, and face, etc., only the elimination positions.

(b) Only the user's elimination positions are view for health problems.

(c) A camera's view of a body isn't analysed by a computer for health problems.

(d) A camera doesn't use optical zoom, it only uses computer zoom (e) A camera angles view of the user's body isn't always perpendicular, which can lead to distortion of the viewed body area.

(f) Health sensors aren't used to automatically sense a user's health.

(g) Health care provider's don't remotely operate and view a user using a camera.

(h) A computer isn't used to direct a bidets water stream to the user's elimination positions.

(i) Bacteria and virus can be transferred to a user's fingers by touching buttons, which have bacteria and viruses on them, when operating an elimination position viewing camera.

SUMMARY

This summary outlines three embodiments of a toilet body viewing camera.

1. Cameras operated view the user while they are sitting on a toilet. The cameras can be operated by a user or computer The body viewing cameras are helpful in allowing the user to view, on a display, areas of their body that are difficult to view, such as, the back, and posterior. The cameras can view the user's entire body.

2. Health sensors, and cameras measure and diagnose a user's health while they are sitting on a toilet. Health sensors, and cameras can measure and diagnose the health conditions of the user body, such as, blood pressure, blood glucose, and skin cancer, etc. Depending on the health test sensors, and or cameras, health tests can be performed by contacting the user's body, or by non-contact viewing of the user's body. The health results are viewable, on a display viewable by the user.

3. A bidet water stream can be visually directed, by a user, or computer, at the user's elimination positions while they are sitting on a toilet. A camera is attached to a bidet wand, and can view the bidets water stream's contact with the user's elimination positions. The user or computer can use the view of the water stream, to move the water stream to areas on their elimination positions. The visual directing of the water stream allows for a more accurate directing of the water stream on the user's elimination positions. The user can visually view their elimination positions, while streaming water on to them, and after streaming, to be sure that they are being thoroughly washed.

The three embodiments can be combined into one embodiment, such as, the user can view their body on the display with the camera, they can sense or measure their health with the camera and health sensors, and they or the computer can direct the water stream on their elimination position.

The components of the combined three embodiments, include a tablet computer, the tablet computer having a display, an eye tracking input device connected to the computer the computer connected to a motor controller, the computer and motor controller connected to, a camera moving device, a camera attached to the moving device, health sensors attached to the moving device, an electronic bidet, health sensors attached to a toilet seat, a light attached to the moving device, a toilet, health sensor software, body recognition software, genital recognition software, eye tracking software, and system operating software, programmed into the computer, etc.

Accordingly several advantages are to provide an improved visual health monitoring toilet area, a health sensing area, and an improved water aiming bidet, as a means of providing a more sanitary, fun, and healthy self-examination experience for a person.

ADVANTAGES (a) The user can view their back, and posterior.

(b) By viewing their body, posterior and back, a user can possibly detect health concerns in the early stages, and seek treatment for them, before they progress to more serious health problems in the future.

(c) Health tests can be performed by the user, or automatically by the computer. Health test are conveniently preformed in a bathroom environment. Health testing devices are centrally located in one location in the bathroom. The health testing devices aren't misplaced. Remembering to perform health tests is more likely, in a location that the user frequents often, such as, the bathroom.

(d) The computer can automatically visually diagnose possible health concerns viewed on their body, such as, skin cancer, and alert the user to the health concern visually on the display.

(e) The computer can diagnosis areas of their body, by comparing imaged abnormal body areas to a computer data base or an internet data base of visual body ailments, to find a match of the images, and ailments.

(f) Health sensors can passively test the user's blood sugar level, blood pressure, temperature, weight, etc., their isn't need to have body fluids analysed.

(g) The user worries less about their health, by having up to date health information from viewing and health testing their bodies.

(h) The camera can be zoomed optically to produce a superior view of an area, as opposed to a computer zoom which creates a pixilation of the view of the image, and a loss of definition of the image.

(i) The computer can recommended the user seek further health care.

(j) Health test results can be automatically sent, to health care provider for analyses, over the internet.

(k) The computer can automatically scan or view the user's body, following either a user preprogrammed route or a default programmed route.

(l) The transmission of germs to a user's fingers is decreased, by the user operating a camera and health seniors touch freely, with a touch free input device.

(m) The user, or the computer can direct a bidet water stream at their elimination positions, and view how well the water stream is cleaning the user's elimination positions.

A camera for self-examination, is more easy to use, and is in a more comfortable private toilet setting. Self-examination using a camera in a bathroom, is a more comfortable setting then other locations, since people are more accustomed to privately viewing their bodies in the bathroom.

Still further advantages of the improved body camera and health sensors will become apparent, from a study of the following description and drawings.

DRAWINGS

Figures

The drawings, and closely related figures may have the same number but different alphabetic suffixes.

Figure 1:
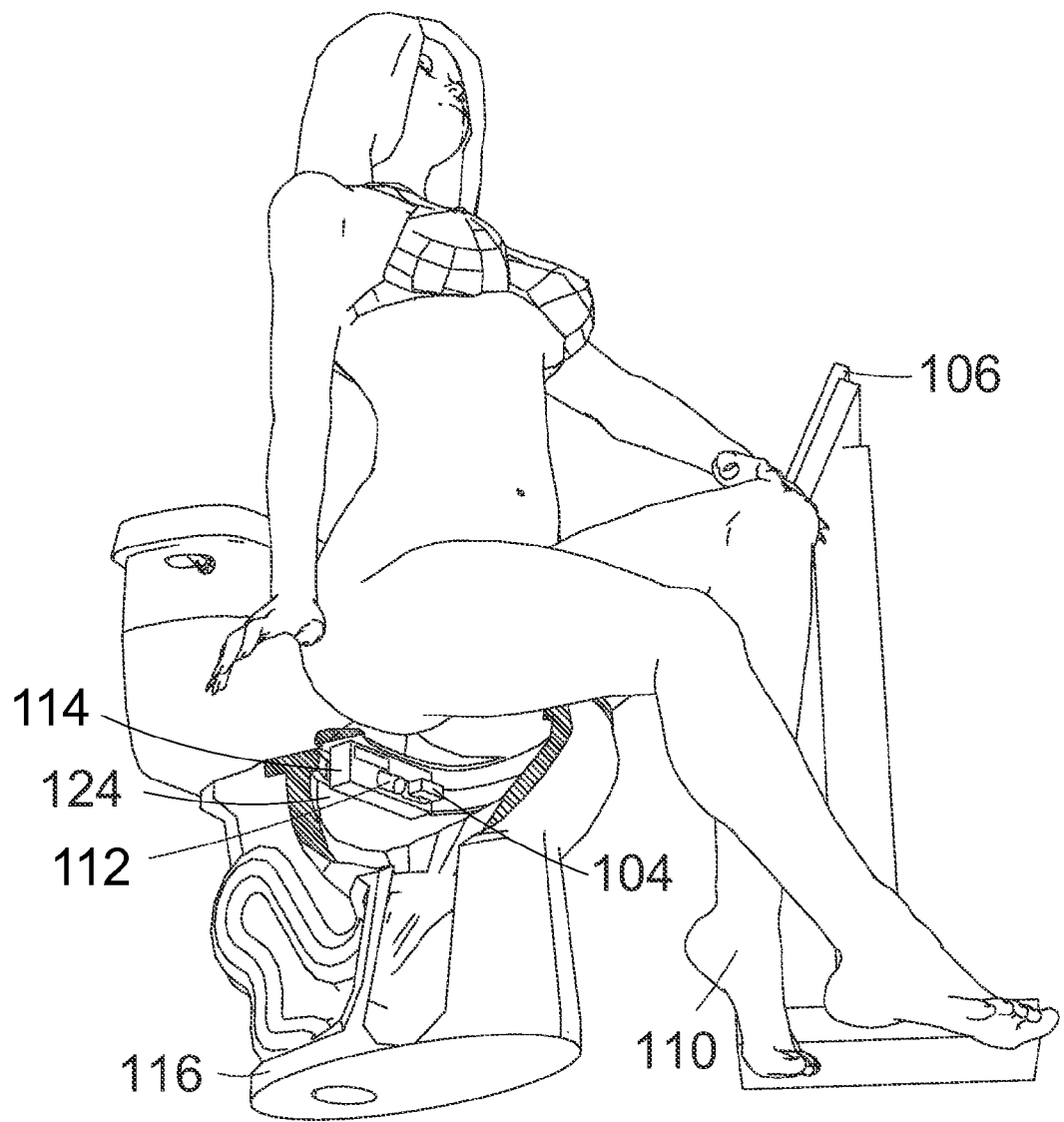
FIG. 1 shows a perspective view of to a camera moving device, inside a toilet bowel, a tablet computer connected to the camera moving device, and a user sitting on a toilet seat.

REFERENCE NUMBERS 102 camera
104 camera moving device or bidet camera wand
106 tablet computer
108 display
110 user
112 bidet wand water
114 bidet
116 toilet
118 lens air drier nozzle and water nozzle
120 cursor
124 toilet bowel
126 toilet seat
128 light
140 back elimination position
142 front elimination position
144 posterior
146 possible precancerous skin lesion
148 genital herpes
150 hemorrhoids
152 ultrasonic distance sensor
154 angle measuring laser
156 user input eye tracking device
158 displayed view
160 rash
164 display alert
166 menu
168 highlighted health concern
192 heart rate monitor, and blood oxygen saturation monitor
502 camera
506 tablet computer
508 display
524 toilet bowel
530 skin cancer detecting laser
532 blood glucose measuring laser
534 blood pressure sensor
556 a user mid-air gesture recognition camera
562 visual temperature sensor
564 menu icons
566 flexible camera moving device or bidet camera wand
568 body elimination sensor
570 user detection sensor
604 camera moving device or bidet camera wand
606 camera connected to a bidet wand,
608 health sensors, and cameras attached to a toilet seat
702 camera
704 camera moving device
706 tablet computer with display
722 The Raman spectroscopy device
728 light
730 skin cancer detecting light
732 blood glucose measuring laser
734 blood pressure sensor
738 malaria detector 752 ultrasonic distance sensor
754 angle measuring laser
762 visual temperature sensor
1002 camera
1004 camera moving device
1006 tablet computer
1008 display
1022 electrocardiogram EKG
1026 toilet seat
1028 light
1030 skin cancer detecting laser
1032 blood glucose measuring laser
1034 blood pressure sensor
1038 heart rate monitor, and blood oxygen saturation monitor
1056 mid-air hand gesture recognition camera
1062 temperature sensor
1070 feet weight scale
1072 seat weight scale
1074 Kinect camera
1076 Electrical impedance sensors
1078 health results shown
1202 camera
1208 display
1290 3D lasers
1292 camera attaching device
1302 camera
1304 camera and laser device
1306 Hololens 3D display
1380 body imaging laser
1382 body rail
1402 camera
1404 camera and laser device
1484 rotating floor disc
1486 joystick
1488 health sensors
1602 camera,
1604 camera moving device or bidet camera wand
1612 bidet wand water
1616 toilet
1618 lens and ultrasonic sensor air drier nozzle
1608 display
1614 bidet
1620 cursor
1622 water stream
1624 toilet bowel
1628 light
1640 back elimination position
1642 front elimination position
1652 ultrasonic distance sensor
1656 a user mid-air hand gesture recognition device
1696 bottom air dryer nozzle
1902 cameras
1904 toilet seat lid
1906 computer
1908 microphone
1910 LED lights

DETAILED DESCRIPTION FIRST EMBODIMENT

A Movable Camera Used for Viewing a User's Posterior Description

Figure 2:
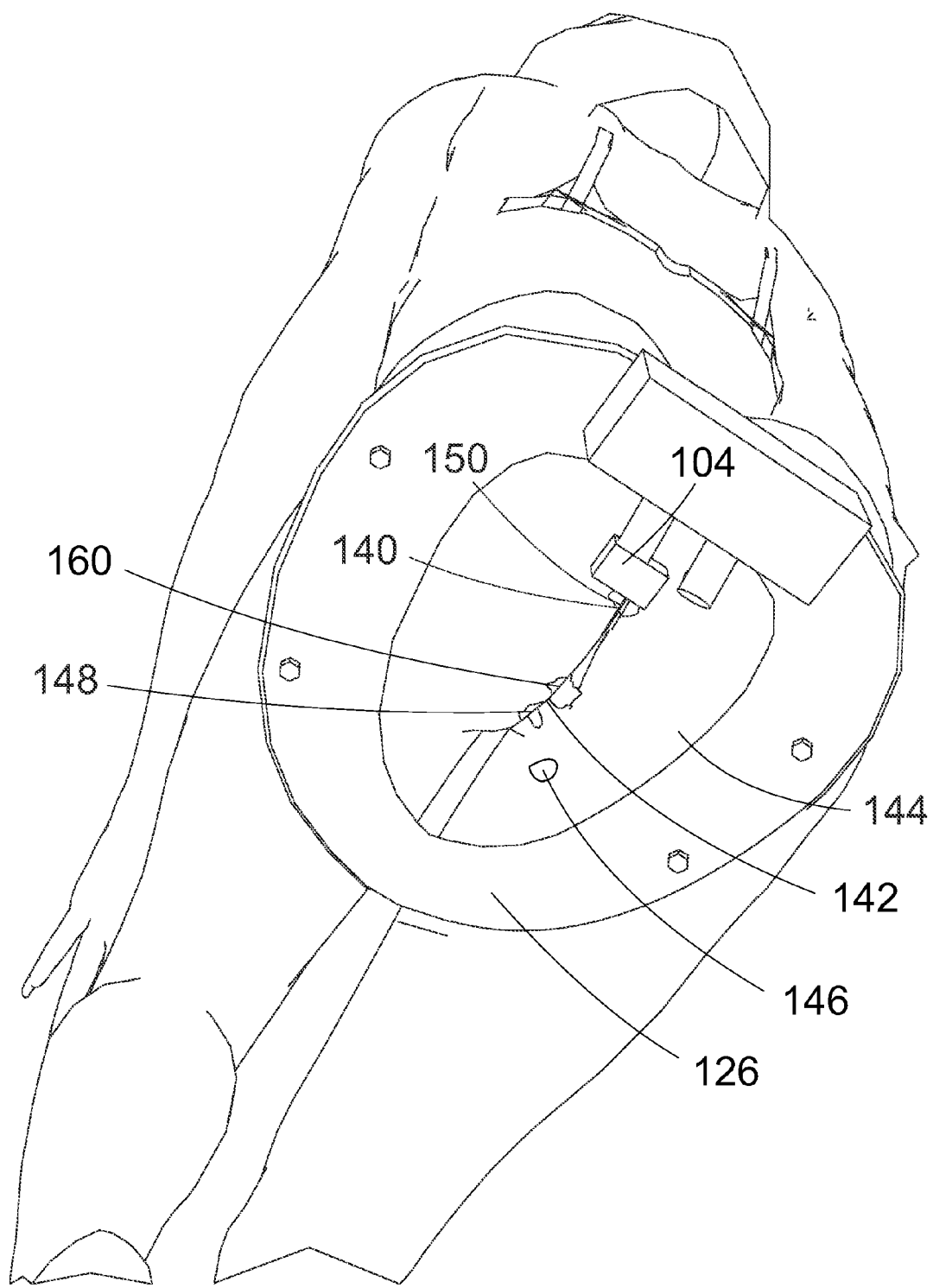
FIG. 2 shows a perspective view of a camera moving device, and a user sitting on a toilet seat.
Figure 3:
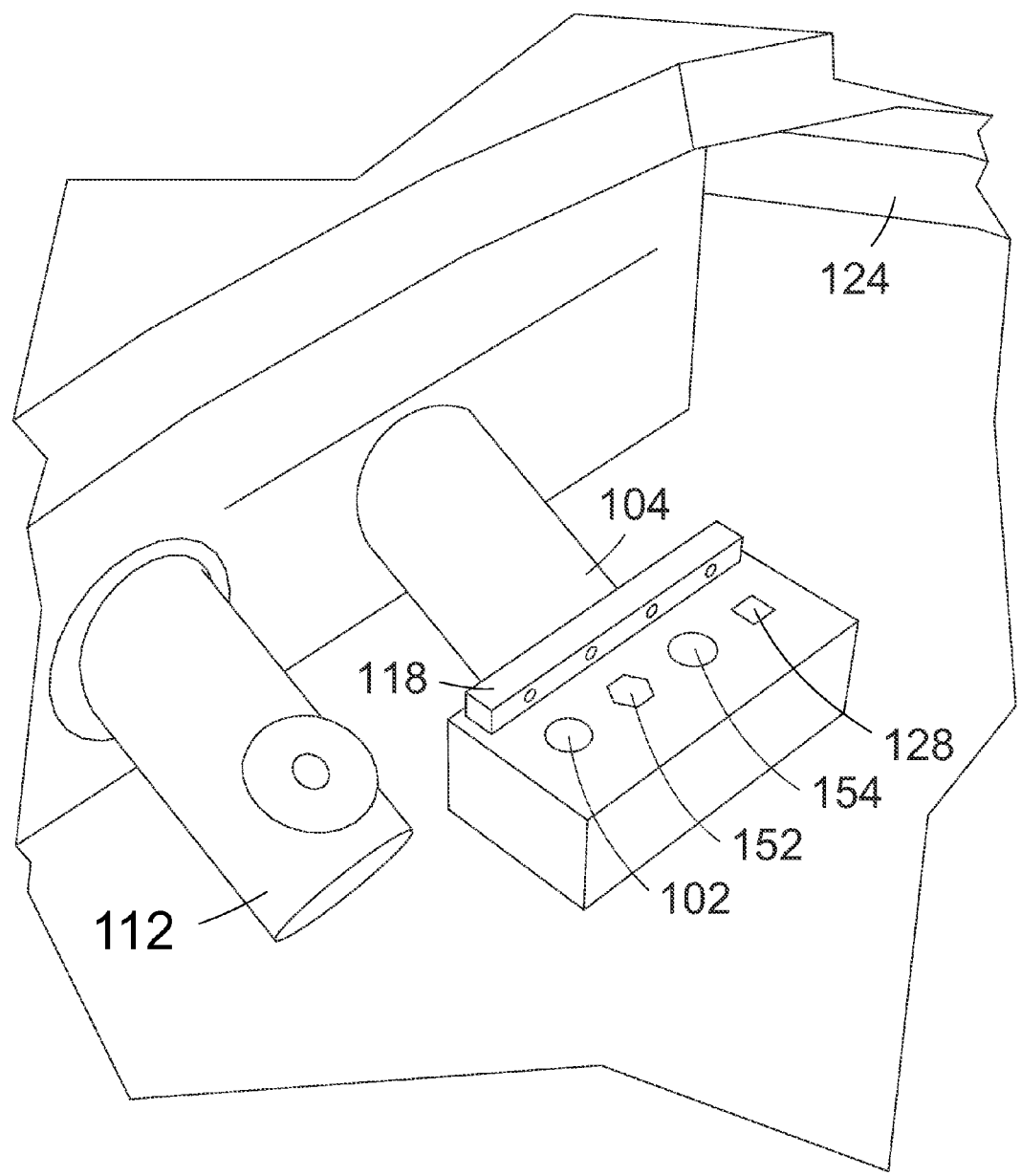
FIG. 3 shows a perspective view of a camera moving device connected to a bidet inside a toilet bowel, a camera, a ultrasonic distance sensor, a light, and health sensors, attached to the camera moving device.
Figure 4:
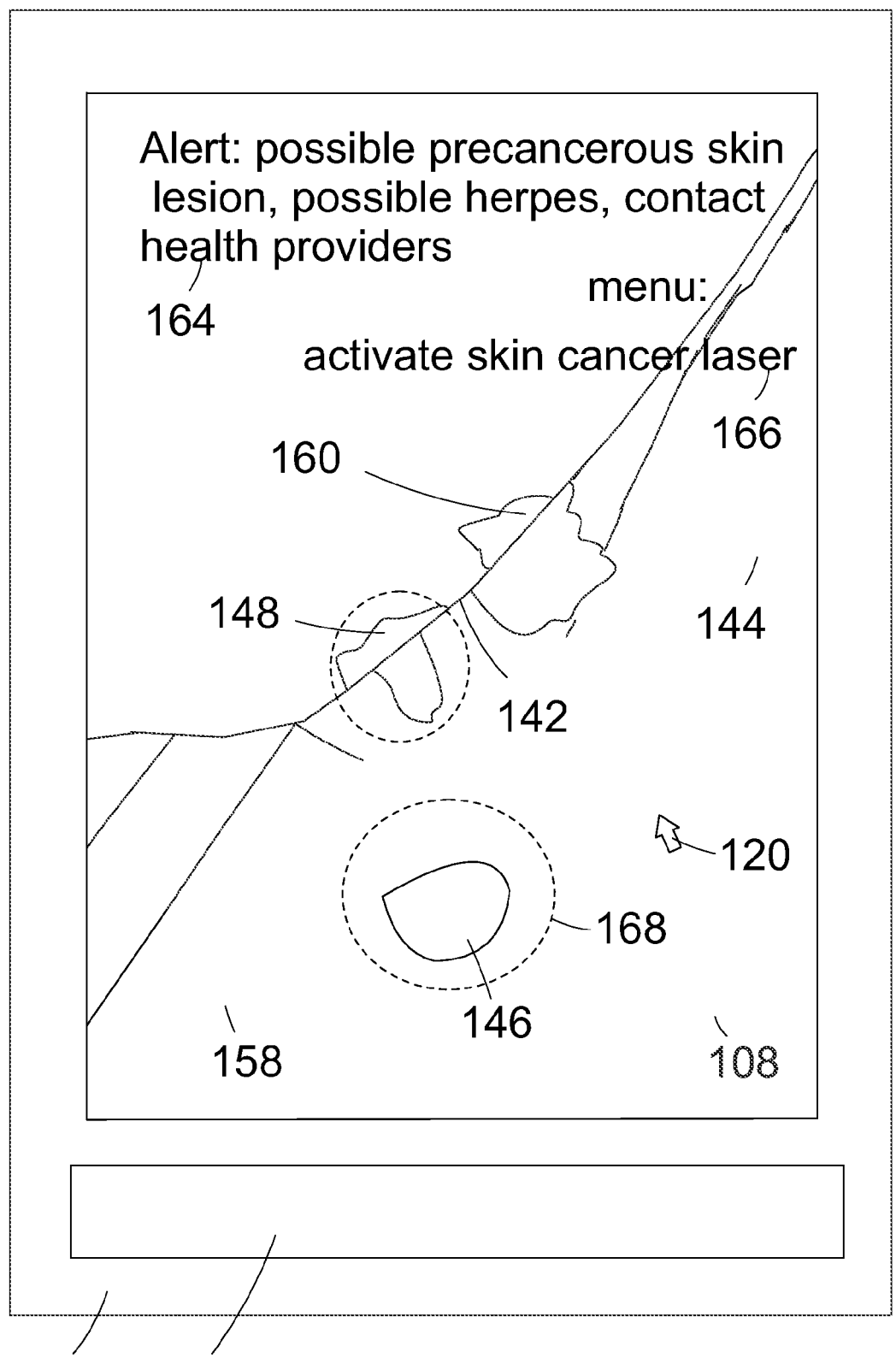
FIG. 4 shows a front view of a tablet computer, an eye tracking sensor attached to the computer, a display, the display showing a user's posterior, highlighted health ailments on the posterior, text health alerts, a menu, and a cursor

A camera 102 view's a user's posterior 144, from inside a toilet bowl 124, when they sit on a toilet seat, as illustrated in FIGS. 1, 2, 3 and 4. The view of their posterior is shown on a display, as illustrated in FIG. 4. The display is viewable by the user 110. Software for visually identifying health problems, such as, skin cancer 146, herpes 148, skin rash 160, hemorrhoids 150, is programmed into the computer, as shown in FIGS. 2 and 4. The computer has a visual data base of health ailments. The computer connects a visual data base of health ailments on an internet, or internet cloud.

Camera

The video camera is connected to a tablet computer 106, and a motor controller (not shown), and attached to a bidet wand or camera moving device 104. Heath sensors are attached to the bidet wand, and connected to the computer. A second bidet wand sprays water at the user's elimination positions 140, 142. In and other embodiment a bidet could have one wand which streams water to the user, and a camera and heath sensors attached to the wand.

A light 128 is connected to a motor controller. The light is attracted to the wand. The motor controller is connected to the computer. The motor controller is connected to a building alternating current power supply source (not shown).

The camera lens 102, is a par focal lens. The camera, and camera lens is water proof. A bidet connects to the bidet wand. The bidet connects to the computer.

The camera lens is positioned in the wand 104 to view the user's posterior, when the user is sitting on the toilet 1116. The wand incorporates the camera 102, the camera lens, an air nozzle drier 118, a lens water flushing nozzle 118, a camera angle measuring laser 154, and an ultrasonic distance sensor 152.

The camera 102 can use two dimensional 2D, and or three dimensional 3D imaging of the user. The camera's software, is programmed into the computer. Three dimensional cameras can be used, such as, an Intel real sense camera, and real sense software, a Kinect technology camera sensor made by the PrimeSense company, a Cambord Pico made by the Optoma Company in the United Kingdom, a Kinect camera made by the Microsoft company, or a XTR3D camera made by the Creative Reality company, in Israel.

The computer 106 comprises a processor, the processor is programmed with a system operating software. The processor is connected to a memory for storing and retrieving data.

For brevity when referring to the devices connection to the computer, it is implied that the devices and the computer communicate with each other. The devices are also connected to the motor controller, which supplies electrical power to the device and or devices.

User Input Device for Moving the Camera

A touch free user input device is connected to the computer. The input device is an eye tracking input device 156, made by the Tobii Company, and is connected to the computer. Other touch free user input devices can be used such as, mid-air hand gesture devices like a Leap made by the Leap Company, or an Intel realsense mid-air hand gesture camera. Voice recognition for voice commands can be used for user input. A microphone can be connected to the computer, or a microphone built into the tablet can be used hear the voice commands. The computer can be programmed with voice recognition software. Touch free software associated to the touch free input device used, is programmed into the computer. A user thought input device, made by the Emotiv Company, can be connected to the computer. A joy stick can be connected to the computer. A touch screen can be connected to the computer.

Bidet Wand

The bidet camera wand or camera moving device 104 is connected to the computer, and the motor controller. The bidet camera wand is attached to motors or linear actuators (not shown).

The computer is programmed, with bidet wand positioning software. The bidet can be temporarily attached to the toilet. The bidet's temporary attachment, allows the bidet to be detachably connected to the toilet, or other toilets a multiple amount of times. The bidet can be permanently attached the toilet 116. The camera moving device 104 is spring loaded, and will move if the user's movements contacts the wand.

Camera Distance

An ultrasonic distance sensor 152, is attached to the camera moving device wand. The distance sensor could also be a laser distance sensor, or an optical distance sensor, etc. A distance measuring software is programmed into the computer. The sensor can also be used to detect the presence of a user's presence on the toilet seat.

Camera Angle

A camera angle measuring Laser 154 is attached to the bidet wand. The camera angle measuring Laser is connected to the computer, and the motor controller. A camera angle measuring software is programmed into the computer. The computer is programmed with software to detect the lasers angle.

Display

The display and computer are part of the tablet computer. In another embodiment, a camera could be connected directly to a display, by-passing the computer. A user input eye tracking device 248 is connected to the tablet. The display can be a liquid crystal display LCD, or plasma display, etc. Camera video storage is connected to the computer. The tablet computer is a waterproofed tablet, and is made by the Sony Company.

The displays shows an interactive menu 166, in FIG. 4. Menu items include, move camera, zoom camera in and out, record views, connect to internet, network video conference, skype, send video over internet, light intensity increase or decrease, etc. Health alerts 164 are show in different colors on the display. Detected health concern are highlighted 168 on the display, in different colors. The color is associated to the color of the health alert text color, so the user can associate the alert color with the heighted health concern.

The computer 106 can connect to the bidet with a wireless connection, by using radio wave signals, such as, Bluetooth radio waves, WIFI radio waves, and a direct WIFI radio wave connection, etc. The tablet can connect to the bidet using a wired connection. The tablet computer 106 can be attached to a toilet arm rest, a tablet stand, or it can be used unconnected.

Keeping the Camera Lens Unobstructed

An air nozzle 118 and water nozzle 118 is adjacent to the camera lens. The air and water nozzle connects to an air pump inside the bidet housing. A water pump is inside the bidet housing 114. An air and water valve connects to the computer. The air and water pump are connect to the computer.

Safety features include using a ground fault circuit interrupter GFCL. The GFCL is an electrical device that disconnects a circuit whenever it detects, that the electrical current is not balanced between the energised conductor and the return neutral conductor. Such an imbalance may indicate current leakage, through the body of a person, who is grounded and accidentally touching an energised part of the circuit. The GFCL are designed to disconnect quickly enough, to prevent injury caused by such shocks.

When the word connected is used, in the reference to electrical devices, it's implied that the electrical components, are connected by electrical wire and or information conducting, communicating wire. Other components may use other connections, such as, components which are attached by a physical connection, or connected by radio waves, etc. The bidet system uses a connection to a building water supply, to supply water to the bidet water system.

Means

The computer means is the processer connected to a storage, for analysing data and storing data. The computer means, is the computer programmed with system operating software, bidet wand moving software, user eye tracker input analysing software, and camera imaging recording and displaying on the display software.

The user camera moving means is the user input operated eye tracker, which is used for signaling the computer to move the camera over the posterior. The camera moving means is the camera attached to the movable bidet wand. The health sensor means is the health sensor. The display means is the display. The imaging device means is the camera. The bidet means is the bidet. The toilet means is the toilet.

Software

The processor may be capable of executing program instructions, (e.g. compiled or non-compiled program logic and/or machine code) stored in data storage to carry out the various functions described. The data storage, may include a non-transitory computer readable medium, having stored thereon program instructions that, upon execution by client device, cause client device to carry out any of the methods, processes, or functions disclosed in the specification and/or the accompanying drawings. The execution of program instructions by processor may result in processor using data.

The device may further include on-board data storage, such as memory coupled to the processor. The memory may store software that can be accessed and executed by the processor, for example. The host may be any type of computing device or transmitter including a laptop computer, a smart phone, etc., that is configured to transmit data to the device. The host and the device may contain hardware to enable the communication link, such as processors, transmitters, receivers, antennas, etc.

Communication Link

A radio transmitting and receiving device (not shown) for connecting to the internet is connected to the computer, such as, Wi-Fi device or cell phone device has The WIFI device connects to the internet using Wi-Fi radio frequencies to connect to WIFI internet router which is connected to the internet.

For example, the communication link may be a wired link via a serial bus such as USB, or a parallel bus. A wired connection may be a proprietary connection as well. The communication link may be a wireless connection, such as Bluetooth, IEEE 802.11 (IEEE 802.11 may refer to IEEE 802.11-2007, IEEE 802.11n-2009, or any other IEEE 802.11 revision), or other wireless based communication links. In another example, the system includes an access point through which the device may communicate with the internet. In this example, the device may not require connectivity to the host. The access point may take various forms. For example, if the device connects using 802.11 or via an Ethernet connection, the access point may take the form of a wireless access point (WAP) or wireless router. As another example, if the device connects using a cellular air-interface protocol, such as a CDMA or GSM protocol, the access point may be a base station in a cellular network that provides Internet connectivity via the cellular network. As such, the device may include a wired or wireless network interface through which the device can connect to the access point. As an example, the device may be configured to connect to access point using one or more protocols such as 802.11, 802.16 (WiMAX), LTE, GSM, GPRS, CDMA, EV-DO, and/or HSPDA, among others. Furthermore, the device may be configured to connect to access point using multiple wired and/or wireless protocols, such as "3G" or "4G" data connectivity using a cellular communication protocol (e.g., CDMA, GSM, or WiMAX, as well as for "Wi-Fi" connectivity using 802.11). Other examples are possible. Alternatively, the host may include connectivity to the internet, and thus, the device may access the internet through the host.

Software Storage

The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may include non-transitory media, such as secondary or persistent long term storage, like read only memory (ROM), optical or magnetic disks, compact-disc read only memory (CD-ROM), for example. The computer readable media may be any other volatile or non-volatile storage systems. The computer readable medium may be considered a computer readable storage medium, for example, or a tangible storage device. The display shows camera functions icons, such as, move camera, zoom camera in and out, record views, and activation icons.

Programming the Computer

A Kinect for Windows software developer's kit or Microsoft Robotics Developers Kit can be used to program the computer 106 for the Kinect sensor. An Intel perceptual computing software developer's kit could be used to build applications for the automatic bidet. The Microsoft Software Developers Kit can be used to build automatic bidet function applications. Various programming languages can used to program the computer 106 such as C++, C#, and Microsoft Visual Studio Ultimate, FAAST key mapping software, Microsoft Visual Programming Language, Microsoft NET 4.0 XNA 4.0, Silverlight 4.0, and Visual Basic.NET. The Microsoft Software Developer's Kit allows developers to write Kinect applications in C++/CLI, C#, Microsoft Visual Programming Language, or Visual Basic .NET. The Microsoft Robotics Developers Studio application contains a graphical environment, Microsoft Visual Programming Language: (VPL) command line tools which may allow a developer to deal with Visual Studio projects (VS Express version) by possibly using C#, and 3D simulation tools.

The computer 106 may be programmed using, an Intel software developer's kit, a Microsoft windows commercial software development kit, or Linux operating system, or Android operating system, or Blackberry operating system, or apple operating system. Computer program code for carrying out operations of the object detection and selection mechanism may be written in any combination of one or more programming languages, including an object oriented programming language such as Java, Smalltalk, C++ or the like and conventional procedural programming languages, such as the "C" programming language or similar programming languages. The program code may execute entirely on the computer, partly on the computer, as a stand-alone software package, partly on the computer and partly on a remote computer or entirely on the remote computer or server. In the latter scenario, the remote computer may be connected to the computer through any type of network, including a local area network (LAN) or a wide area network (WAN), or the connection may be made to an external computer (for example, through the Internet using an Internet Service Provider).

Flowchart

The object detection and selection mechanism is described below with reference to flowchart illustrations and or block diagrams of methods, apparatus (systems) and computer program products according to implementations thereof. It will be understood that each block of the flowchart illustrations, FIG. 20, and or block diagrams, and combinations of blocks in the flowchart illustrations and/or block diagrams, can be implemented or supported by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The computer program instructions may be loaded onto a computer or other programmable data processing apparatus, to cause a series of operational steps to be performed on the computer 106, or other programmable apparatus to produce a computer implemented process, such that, the instructions which execute on the computer 106, or other programmable apparatus provide processes, for implementing the functions or acts specified, in the flowchart and or block diagram block or blocks.

Figure 20:
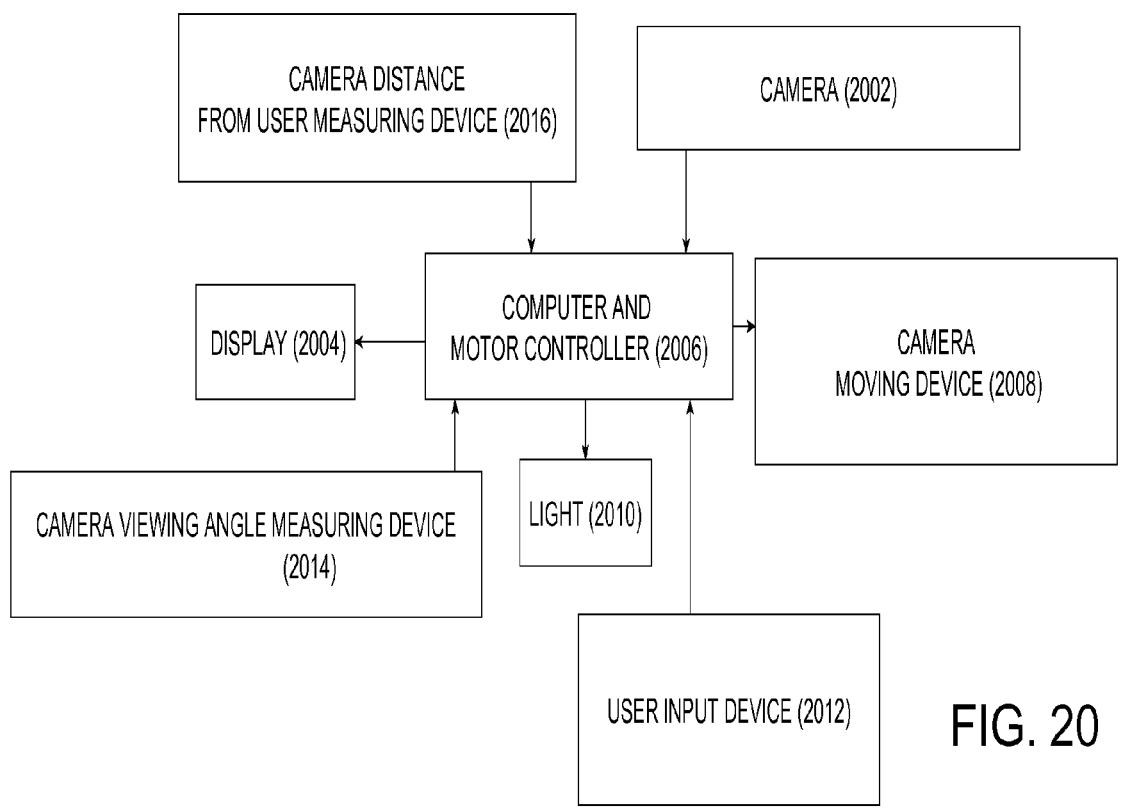
FIG. 20 illustrates a block diagram of hardware connections between components of a movable user health detecting camera.
Figure 21:
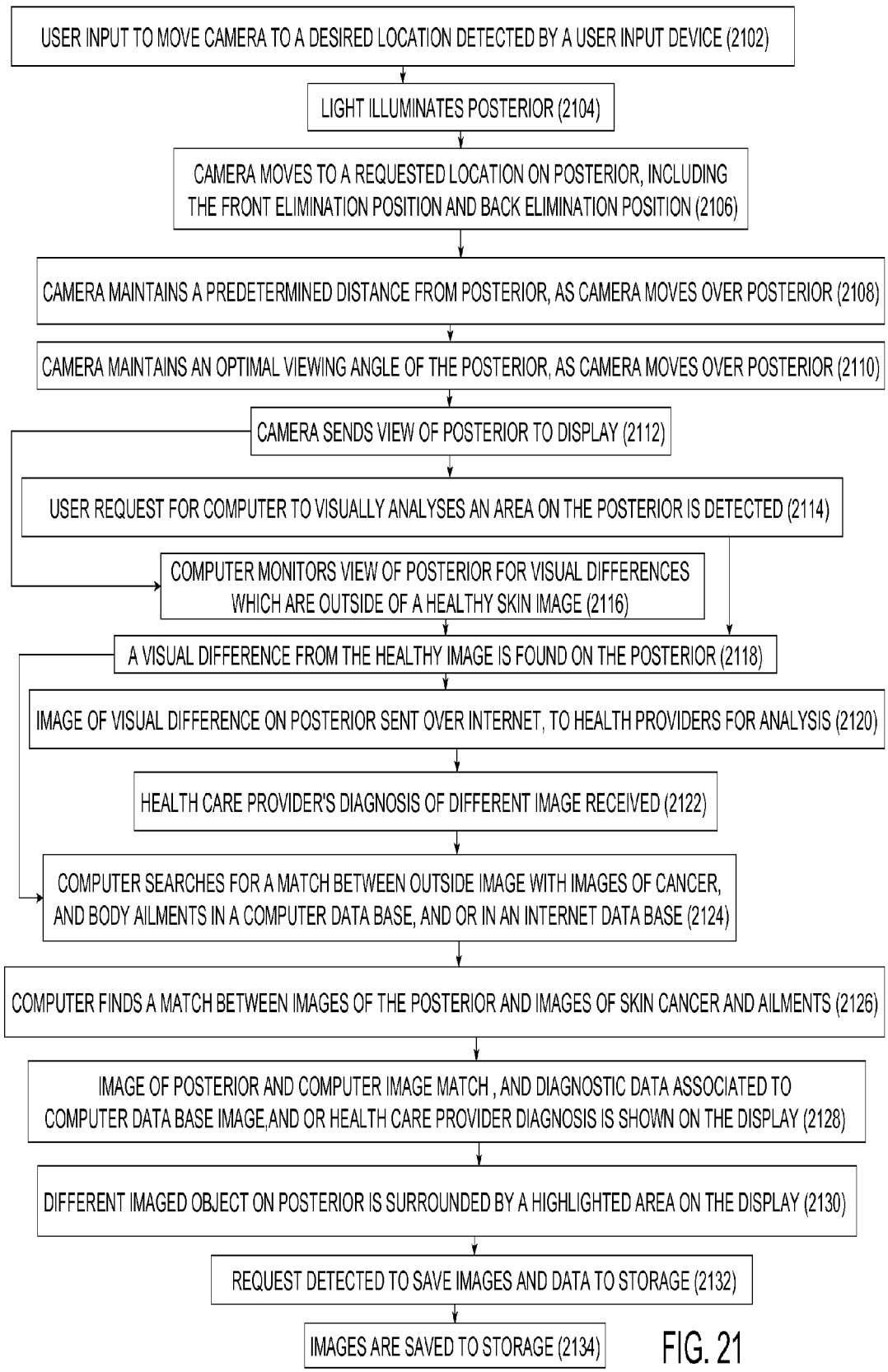
FIG. 21 depicts a software flowchart of a movable user health detecting camera, and health sensors.

FIG. 20 is a flowchart illustrating a method of operating a user operated posterior viewing and health sensing camera. Software steps of the bidet operation, may include some of the following steps, user input to move camera to a desired location detected by a user input device (2102), camera moves to a requested location on posterior, including the front elimination position and back elimination position (2106), camera maintains a predetermined distance from posterior, as camera moves over posterior (2108), camera maintains an optimal viewing angle of the posterior, as camera moves over posterior (2110), user request for computer to visually analyses an area on the posterior is detected (2114), computer monitors view of posterior for visual differences which are outside of a healthy skin image (2116), a visual difference from the healthy image is found on the posterior (2118), image of visual difference on posterior sent over internet, to health providers for canalisation (2120), health care provider's diagnosis of different image received (2122), computer searches for a match between outside image with images of cancer, and body ailments in a computer data base, or in an internet data base (2124), computer finds a match between images of the posterior and images of skin cancer and ailments (2126), image of posterior and computer image match, and diagnostic data associated to computer image, and or health care provider diagnosis is shown on the display (2128), different imaged object on posterior is surrounded by a highlighted area on the display (2130), request to save images and data to storage (2132), images are saved to storage (2134)

Block Diagram

FIG. 20, illustrates a block diagram of some of the hardware components connections of the device, camera (2002), display (2004), computer and motor controller (2006), camera moving device (2008), light (2010), user input device (2012), camera viewing angle measuring device (2014), camera distance from user measuring device (2016).

In addition, for the method and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process.

In the detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

A User Movable Camera Used for Viewing a User's Posterior on a Display Operation The user uses the camera 102 to view their posterior 144, for signs of possible health problems, and to view areas of their body which are difficult to view. The view of their elimination positions can be used to see how well the bidets water stream has washed their positions. If the user visually detects that their positions haven't been completely washed, the user can rewash their positions. The user can view their position while water is being streamed on them. The heath sensors preform health tests on the user's body.

The user sits on the toilet seat 126. The light 128 activates and illuminates the user's posterior, and elimination positions, illustrated in FIG. 2. The camera activates, and views the user's posterior. The view of the user's posterior, genitalia and elimination positions is shown on the display 108. The view is viewable by the user. The user moves the camera's viewing area, to desired viewing areas over the posterior, and viewable area of the legs. The user moves the camera to a desired view of the posterior. The camera continually sends real time video images of the posterior to the display. The display shows the changing view of the posterior in real time.

Computer Diagnosis of Ailments

As the user move the camera over the posterior, the computer analyses the images for matches with images of skin cancer, or other ailments, in the computer's visual data base of ailment, or to a data base of ailment on the internet, or the internet cloud. The computer identifies objects on the skin that are abnormal looking, which are outside of a preprogrammed visual profile of healthy skin. When visual health problems are detected the user is alerted to the problem by a visual alert on the display.

Health alerts 164 are shown in text on the display. The text alert is associated to a highlighted 168 on the user's body. The association allows the user to view the health alert, and locate the associated alert on the body. The health alerts and associated highlights alerts, are in the same color. The same color can be in colors, and shapes, such as, red, green, blue, circle, and triangle, etc.

User Input Device for Moving the Camera

The eye tracker has a view of the user's eyes. The eye tracker tracks the eyes. The eye movements are interpreted, as user input by the eye tracker. The user turns one of the menu items of the system on by moving a cursor 120, with their eye movements, to a menu item they would like to activate. The user holds their view on the cursor on the item, and the item is click activated. The user eye tracking sensor 156 is continually activated.

For example, the user moves their eyes in view of the eye tracking sensor, to move the camera 102 forward, which moves the view of the posterior, on the display, to a more forward position. Using the eye tracking sensor, the user moves the displayed cursor to the left of the posterior, and stops the cursor at an area they want the cameras view to move to, the view moves to the left side following the cursor and stops when the cursors movement stops.

For a different view the user then moves the displayed view to the right side of the user's back elimination position. The user moves the view back ward and to the right side. The user zooms into the elimination position, creating a magnified view of the viewed elimination position, on the display. The user analyses the video images of their posterior on the display, for signs of possible health concerns. The user is reassured that they have examined their posterior.

The user uses the displayed view 158, to discern how much eye input into the eye tracking sensor they need to move the camera's view to an area. They use the view of the cameras view of their body to guide the movement of the camera's view, using the eye tracking sensor.

By viewing on the display where they want the camera to move with their eyes the user can rotate the wand right and left, the camera can tilt or rotate forward and backward, extend and retract the bidet wand, move the wand to the right side and to the left side, and move the wand up and down.

The computer instructs the motor controller to supply power or a voltage to the light 128. The motor controller receives the instructions from the computer 106 to power the light. The motor controller sends power to the light. The light illuminates when receiving power from the motor controller. The computer sends instructions to the motor controller to supply power or the camera moving device 104, or the camera, etc. The components are powered and operated by power from the motor controller, and operating instructions from the computer.

The bidet 114 has a motor controller. The computer instructs the motor controller to supply a voltage to the bidet wand motors and actuators, to move the wands. In another embodiment the computer could communicate with, a bidet that has a computer in the bidet, and have the bidet's computer, instruct the bidet motor controller, to supply the voltage, to the bidet devices.

Camera

The camera 102 can be zoomed optically to produce a superior view of an area, as opposed to a computer zoom which creates a pixilation of the view of the image, and a loss of definition of the image.

The camera lens 102, is a par focal lens which uses optical zoom that changes the lens focal length distance. The par focal lens maintains focus while being zoomed in or zoomed out, as its focal length changes.

The camera can digitally zoom in and out to enlarge or decrease the view of the user's posterior. Digital zoom is accomplished by the computer cropping an image down to a centered area with the same aspect ratio as the original. The zoomed digital photographic or video image's quality is reduced.

The lens has a lens cover (not sown) made of a see through covering, such as, Gorilla Glass, or Safire, etc., which protects the lens from wear.

The camera could use a varifocal lens, whose focus changes as the lens zooms in or zooms out, and have the computer refocus the lens, to a clear focus view, as its focus changes while zooming. The camera can optically and digitally zoom in and out to enlarge or decrease the view of the user's posterior Bidet Wand The motors or linear actuators can move the wand from right to left, pivot left or right, rotate them clockwise or counter clockwise, and move up and down in relations to the bidet. The wands can extend, and retract into the bidet. The wand can move the camera to within a default 5 centimeter of the user's viewable body area, inside a toilet bowel. The camera can contact the user's body, though this may obscure the camera's view.

The wands movements are directed by the user. The user instructs the computer to move the wand to a desired location. The computer directs the bidet to move the wand to the desired location. The non-camera bidet wand moves to stream water to the user's elimination position.

The ability of the user to move the camera to almost any location on the user's posterior, allows the user to clearly view almost any location they desire, on the display 108. The male user can view their anus, back elimination position 140 and penis, front position 142, legs, posterior, and surrounding area. A female user can view their vulva, front position 142 and anus, back position 140, posterior and surrounding area. The user can manually view the front and back elimination positions while they are eliminating, and view the elimination. The user can view water from the bidet being streamed to their elimination positions in real time. A larger area can be viewed to speed the viewing, of an area has been viewed before.

After the user wash has finished, the wands, retracts into the bidet housing 114. Inside the housing, the bidet wash wands are washed and sterilized. After the wands are washed and sterilized inside the bidet housing, the wands extend from the housing and are ready, for the next viewing, and wash cycle.

The wands will move when contacted by the user to avoid possible discomfort to the user, and to avoid damage to the wand.

Camera Distance

The ultrasonic distance sensor 152, allows the computer to measure the camera wands distance from the user. The measured distance allows the computer to move the camera and maintain an optimal, and or pre-set viewing distance from the user's body, and to avoid the camera's contact with the user's body while moving the camera. The sensor 152 keeps the camera wand, at a minimum distance from the user, while moving and stationary, to avoid contact with the user.

The user can move the camera's view over their posterior, and view their posterior on the display 108. The assembled bidet components allow the user to visually examine their posterior while they are sitting on the toilet seat. The user's exposed posterior, includes the user's genitals, and front 142 and back elimination 140 positions.

The camera can scan, view the entire viewable area of the user's posterior, by moving over small or large areas of the posterior. The camera can view a 4 centimeter by 3 centimeter viewing area as it moves over the posterior. The view area can be enlarged, by the user, by increasing the distance of the camera lens from the posterior, or decreasing the zoom of the lens, or both. The view area can be decreased, by the user, by decreasing the distance of the camera lens from the posterior, or increasing the zoom of the lens, or both. The viewing area is shown on the display.

Camera Angle

The angle detecting laser 154 measures the camera angles view of the user. The computer is programmed with software to detect the lasers angle.

The computer adjusts the cameras viewing angle as it moves over the posterior, to maintain a perpendicular viewing angle of the posterior area. The camera's viewing angle changes as it view moves over the changing angles and curves of the posterior. The computer moves the cameras angle to maintain a 90 degree viewing angle of the viewed area. The computer moves the camera to compensate for the bodies changing view angle, and to maintain a perpendicular view of the area being viewed.

The camera's perspective view distortion is reduced by maintaining a perpendicular viewing angle of the posterior skin. The camera view angle is perpendicularly maintained to a viewed area, which allows the image to be free of lens position and orientation distortion. As the camera moves over the posterior and the camera angle view changes in relationship to the posteriors curves. The computer moves the camera's viewing angle to compensate for the posteriors curves.

The best camera angle may not always be perpendicular, such as, when the user is eliminating, it is best that the camera is viewing the elimination at an angle instead of from perpendicular directly below the elimination. The computer adjust the angle for the best view.

Other angle measuring sensors, may include, an ultrasonic angle measuring device. The computer uses camera angle measuring software to measure the camera's viewing angle.

Other Sensors for Imaging the Posterior

Other sensors which can also be used for imaging the user's posterior, genitals, front and back elimination positions can be a, Epileptic Labs ultrasonic 3D sensor Epileptic Labs software, made by the Epileptic Labs Company of Sweden. The sensor software, is programmed into the computer Other three dimensional sensors could be used, such as, a Leap sensor, a Kinect technology camera sensor, a Haptix gesture recognition chip, a Primesense sensor, made by the Primesense Company of Israel, a Flutter gesture recognition system, a Infineon 3D Image Sensor IRS10x0C, and infrared sensor, etc.

The user imaging device could be an ultrasonic sensors, an imaging sensor, an imaging device, an infrared camera, an air sonar sensor, and a laser imaging sensor LIDAR, etc.

Posterior Views Shown on the Display

The camera's view of the posterior 158 is shown on the display 108 in color, and is viewable by the user. The display shows the camera's view of the user's body in real time, as the video camera changes it's of view of the user's posterior, and as the camera moves over the posterior. The display can show the images, in different viewing formats, such as, black and white, and infrared, etc.

The video of the user's elimination positions, can be downloaded and saved to the computer storage, or a user's smart phone storage. The user can view the saved images, and playback at a later time. The images can be sent over the internet to health care providers, for their analyses of on the images for health care problems.

Keeping the Camera Lens Unobstructed

The computer detects when the lens becomes obstructed by water or other material. When an obstruction is detected, the computer instructs air or water to be streamed over the lens to remove the obstruction Pressurised air is sprayed out of an air and water nozzle 118 adjacent to the lens, and distance sensor 152. The nozzle directs air over the camera lens covering, and distance sensor, to blow water off the lens, distance sensor, and dry water that might be on the lens cover. The air is pressurised by an electric air pump in the bidet. The air is delivered to the lens by an air hose from the pump, which travels inside the wand 102 to the air spray nozzle. The air can be continuously streamed over the lens.

Water can be streamed out of the air and water nozzles, and can be directed over the lens covering, too clean the lens covering 102. Water is sprayed out of the same nozzles as the air nozzles. A valve allows either water or air to flow through the hose. The value is controlled by the computer. If matter is on the lenses covering, and isn't removed by the air spray, or water rinse, the lens is cleaned by retracting the wand into the bidet and flushing the wand with water. After the lens covering is cleaned, the wand extends to its last location.

Preventative Health

The camera 102 and display 108 allow users to visually become more aware of their bodies, by viewing their bodies on the display. This may help them to have a better understanding of their body, and may increase the energy they expend in maintaining good health, which may increase their body's health. Preventative health, saves users from more serious health concerns in the future, by detecting health problems when they are small and manageable, before they grow into more difficult to manage problems. The user can look for moles on the skin for signs of skin cancer, sexually transmitted diseases STDS, herpes outbreaks, hair grooming, yeast infections, and hemorrhoids. Women and men, can self-exam without having to use a mirror, held in their hand to view their elimination positions. The user's anxiety is reduced, by giving them more knowledge about the health of their body. Instead of worrying about unidentified conditions of their body, they have a way to identify the health of the body. Their anxiety is lessened by viewing area of their body, that they had difficulty in viewing on a regular basis, and they formally had hoped were in good shape, now they know how the area looks.

The camera can identify with computer recognition software, blood in urine, and blood in fecal matter, as the urine or fecal matter is eliminated from the user's body. The software looks for blood colored particles in the fecal matter, and by viewing the color of the urine using color analysis, and parasites by matching images of possible parasites with a data base of stored images of parasites.

Alternate Embodiments

Automatically Viewing the User's Posterior Description

Figure 5:
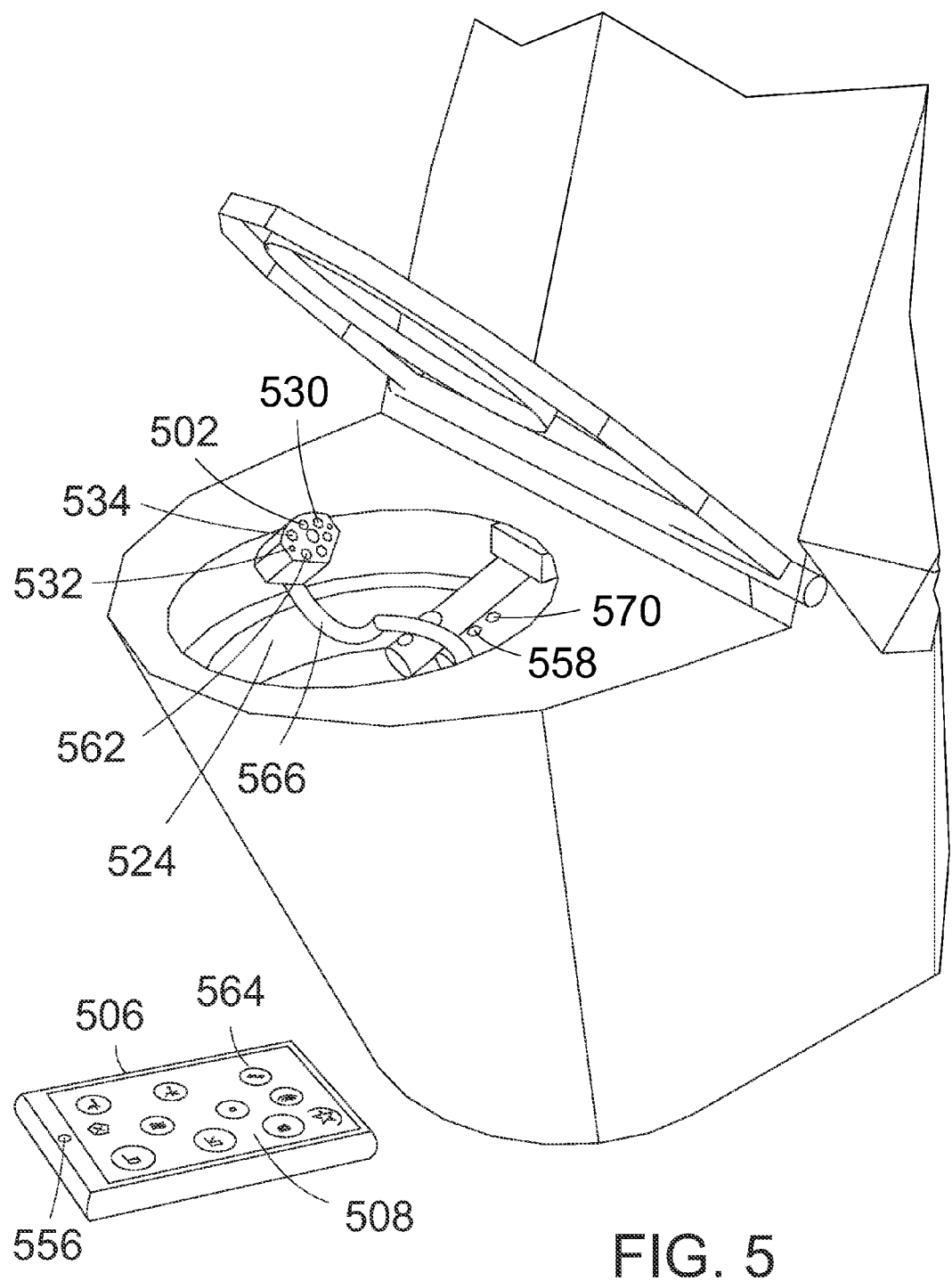
FIG. 5 shows a perspective view of a flexible hose camera moving device, with a camera and health sensors attached to the camera moving device.

A camera is used to automatically view the user's posterior, and the health sensors are used to detect the use's health, as illustrated in FIG. 5. A flexible camera moving device 566 is connected to a computer 506, software to automatically move the camera's view over the user's posterior is programmed into the computer. The flexible hose camera moving device, is attached to the side of the toilet bowel 524. A mid-air hand gesture recognition camera 556 is connected to the computer. A body elimination sensor 568 is attached to a bidet wand, and connected to the computer. A user detection sensor 570 is attached to a bidet wand, and connected to the computer. Menu icons 564 are shown on the display 508.

Health Sensors Attached to the Wand

A skin cancer detecting laser 530 is connected to the tablet computer. The cancer cell detecting laser is used to detect possible skin cell cancers. The laser is made by the Birmingham City University and the University of Central Lancashire, in the United Kingdom. The cancer cell detecting laser is connected, to the computer. The non-invasive system, detects malignant cells by the way in which laser light disperses from them.

A visual blood glucose measuring sensor 532 is connected to the computer. The visual blood sugar detecting sensor is made by the Cnoga Company. The device can determine a user's blood sugar level, from viewing the user's skin's color. A user blood pressure sensor 534, is attached to the camera moving device, and connected to the computer. A visual body temperature sensor 562 is connected to the computer, and attached to the moving device. The visual temperature sensor is made by the Braun Company. A heart rate monitor, and blood oxygen saturation monitor 192 is connected to the computer, is attached to the moving device. Other heath sensor can be attached to the moving device, and connected to the computer, such as, a visual body temperature sensor, and an EKG sensor, heart rate monitor, etc. The camera 502 is attached to the moving device Automatically Viewing the User's Posterior Operation The computer 506 can automatically view the posterior. The user can also activate a pre-set route for the camera to follow on the user's posterior, as illustrated in FIG. 5.

The user sits on the toilet seat. The user is detected by the user detection sensor 570, which could be, an ultrasonic motion detector, the camera, or an infrared user detection sensor. The sensor used to detect a user is continually activated. The light 226 activates and illuminates the user's elimination positions, as illustrated in FIG. 5. The camera activates, and it's view over moves the posterior. The view of the user's posterior, genitalia and elimination positions is shown on the display 508. The view is viewable by the user. As the computer moves the camera viewing area, over the posterior. The display shows the changing view of the posterior in real time. The display shows the camera's view of the user's posterior as the camera automatically moves over and above the user's posterior. The computer directs the moving devices movements.

The user can input activate a default camera viewing route, and have the camera visually follow the route. For example the route could be described as, view front and back elimination positions. The user can touch activate the front and back positions route, by touching a screen icon 564, illustrated in FIG. 5. When the front and back positions route is activated, the camera locates the elimination positions, and follow a front and back positions viewing route. The computer uses genital and back elimination position recognition software to identify the user's front and back elimination positions location.

The computer automatically analyzes the posterior images to detect possible health concerns. If the user's attention to their body is needed, the computer alerts the user, by using the display to show a health alert message. The computer displays a report of its visual analysis of the user's posterior.

Health Sensors

The skin cancer detecting laser 530 is moved over the posterior searching for possible skin cancer. The laser 530 moves over the user's body, and views the user's skin. The laser beam is targeted on skin cells. The cells interact with the beam, and emit a signature spectrum. The patterns are read by a synthesizer which converts the signal into sound, relayed via a speaker. The unique sound is heard if possible cancerous skin cells are detected. The sound for detected cancer cells can be understood by the user, or analyzed by the computer to detect possible cancer cells. The user or computer can identify the unique light patterns and sound thrown off from various forms of cancer. The laser can also be moved to skin objects that the camera finds are outside of the normal skin profile, to analyses the object for possible skin cancer. The camera finds visual object on the posterior, which are outside of a preprogrammed visual normal skin profile. The computer then moves the skin cancer sensor, to view the object to analyse the object for possible skin cancer.

The blood glucose measuring sensor 532 contacts the user's skin, and take a blood glucose measurement. The user blood pressure sensor 534, contacts the user's skin, and take a blood pressure measurement. The visual temperature sensor 562, views the user's body and detects the user's body temperature. The heart rate monitor, and blood oxygen saturation monitor (not shown) is moved to contact the skin, and measures the user's heart rate and oxygen saturation level.

The health sensors are cleaned after each time they are used. The sensors are retracted into the bidet and are washed and sterilized. The sensors are washed after each use by users.

Recording Posterior Images and Health Data

The user touch activates a video record icon on the display 508. The video stream being shown on the display is recorded by the computer. The user can play back the recorded video, at another time.

The user activates the automatic computer viewing of the user front elimination position. The computer automatically moves the camera, and views and displays different moving camera views of the user's front position.

The user can change the pre-set camera distance from the user as travels its viewing route, for example the user may want a close up view of one area and a longer distance view of another viewing area.

The body elimination sensor 568 visually detects if the user is eliminating from their front or back elimination position. The sensor views the elimination positions. If the body elimination detection sensor senses the user is eliminating, the computer moves the moving device to the side of the toilet bowel. The computer waits for 45 seconds after elimination has been detected stopping, and restarts the body scan at the last location that was being viewed when the scan stopped.

The flexible hose camera moving device 566, moves the camera and health sensor to any location on the user's legs, and posterior, inside the toilet bowel.

The user uses mid-air hand gestures within view and 30 cm of the mid-air hand gesture camera 556, to input in to the computer. The user can choose from a menu of different shown input icons on the display.

Additional Alternate Embodiments

Two Camera Moving Devices Health Testing a User's Back Description

Two cameras each attached to separate two camera moving devices, two sensor moving devices, and are located at the rear of a toilet. The rear toilet location is within the camera's viewing distance of the user's back, as shown if FIG. 7. A motor controller supply power to the health sensors. The motor controller is connected to a computer.

For brevity when the camera 702 is used to look for possible skin cancer, its implied skin cancer and other health ailments are looked for, by the camera when viewing the user's body. The other health ailments are described in more detail in this embodiment.

Health Sensors

Figure 8:
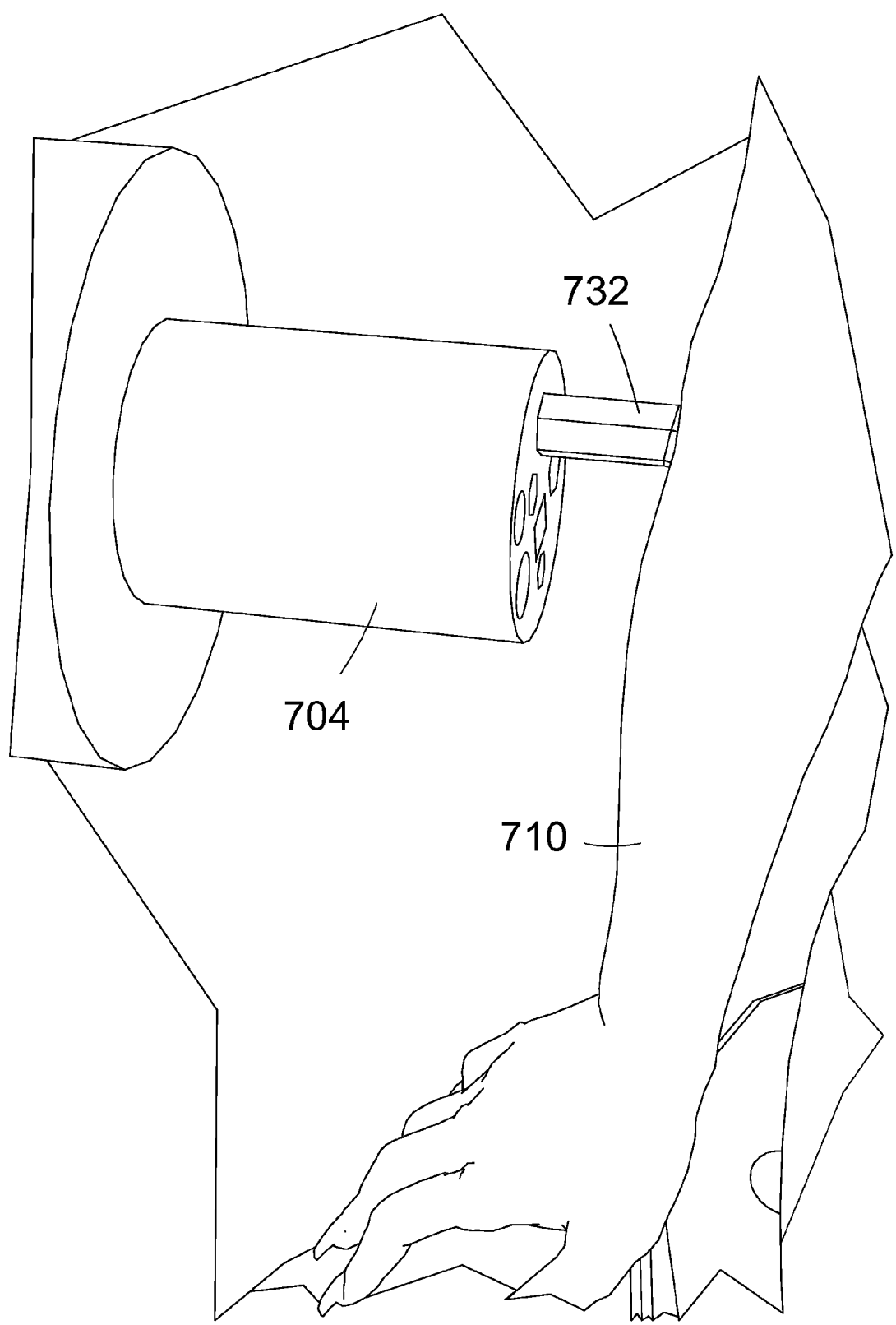
FIG. 8 shows a perspective view of a health sensor contacting a user's arm. The health sensor connected to a camera moving device, incorporated into a curved wall.
Figure 9:
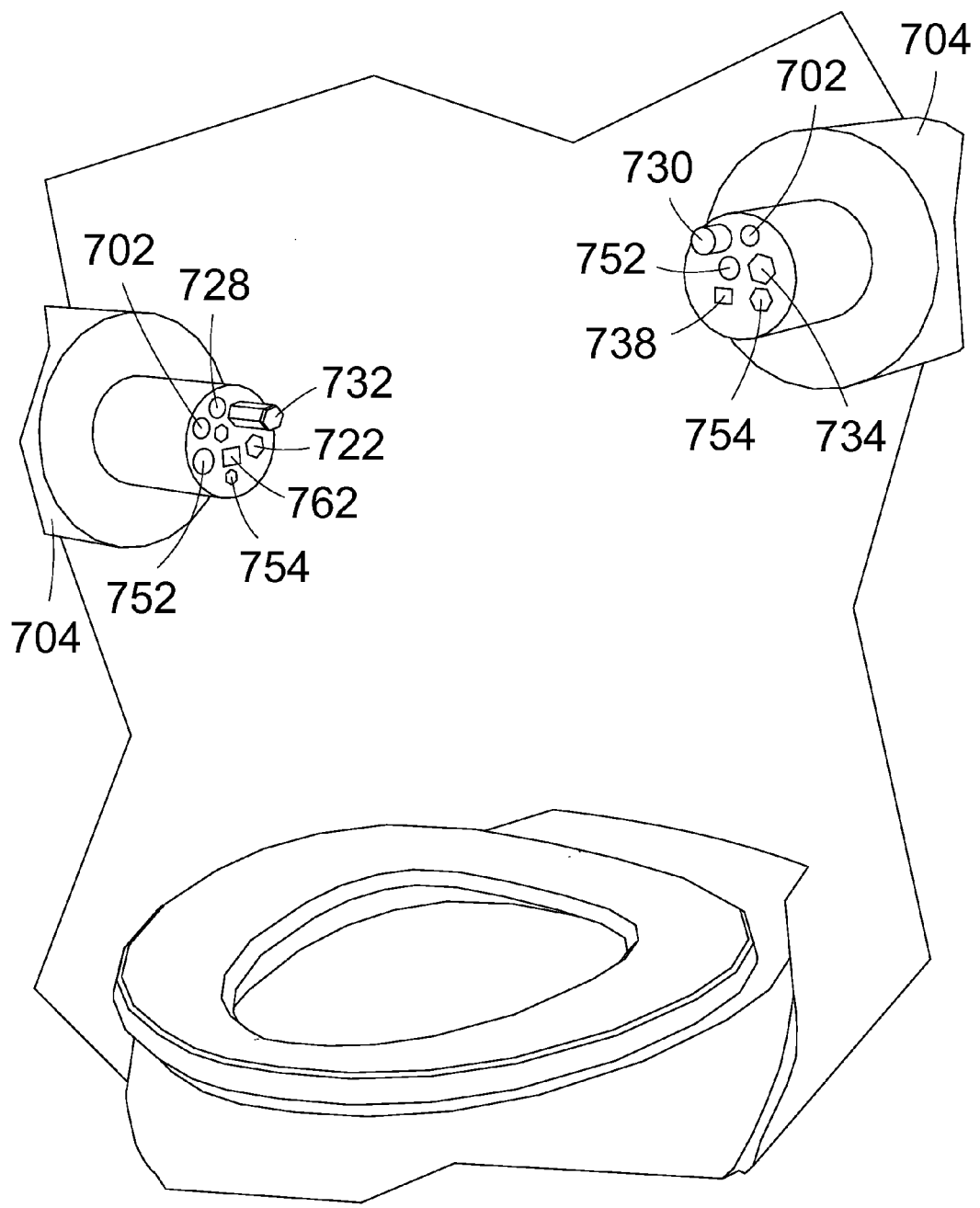
FIG. 9 shows a close up perspective view of a curved wall encompassing a toilet's back and sides, with two camera moving devices attached to the curved wall, each camera moving device having a camera and health sensors incorporated into to them.

Body contacting sensors move to contact the user body parallel to the body, to enable the sensor to be flush with the user's body, as shown in FIG. 8. A skin cancer detecting light 730 is connected to a tablet computer 706, a motor controller, and is attached to the camera moving device, as shown if FIGS. 8 and 9. The skin cancer detecting light, called Verisante Aura, is made by the Verisante Technology Company, of Canada, and detects melanoma, basel, and squamous versions of the disease.

A blood glucose measuring laser sensor 732 is connected to the computer, and the motor controller. The blood glucose sensor is made by the Princeton University Researches.

A user blood pressure sensor 734, is attached to the moving device, and connected to the computer, and motor controller. A Raman spectroscopy device 722, is attached to the moving device, and connected to the computer. A malaria detector 738 made by Rice University in Houston, Tex., is connected to the computer, the motor controller, and attached to the moving device. A visual skin temperature sensor 762, is connected to the computer, the motor controller, and attached to the moving device. A light 728 is connected to the computer, and is used for illuminating the camera's view of the user's back.

The Computer

The computer in programmed, with laser blood glucose analyzing software, laser cancer cell detecting software, EKG software, heart rate and blood oxygen monitor software, skin temperature detecting software, blood pressure machine software, visual body diagnosis, visual skin cancer diagnosis, and camera software, etc.

The computer is programmed with facial recognition software. Genital recognition software can also be programmed into the computer.

The computer is connected to a second display which is viewable by health care providers, the second display (not shown) is located outside of the toilet area, in an area used by the health care providers. The computer is connected to the internet.

The user health testing device sensors may be located at the user's residence, and the care providers remote health test display could be located in a clinic. The user could be in a hospital, or residential care facility, and the care providers could be located on the same premise. The health test and remote display, can be connected to each other over the internet, or a local area network.

Possible Visual Diagnosis of Health Ailments

VisualDx software made by the VisualDx Company is programmed into the computer. The computer is programmed with visual diagnostic software, for diagnosing the camera's view of the user's body, for visual health conditions, such as, Rash, psoriasis, gangrene, chicken pox, measles, Dermatitis, Cold Sores, Hives, Cysts and Skin Lumps, Epidermoid and Sebaceous Cysts, Poison Ivy, Oak, and Sumac, Varicose Veins and Spider Veins, Vitiligo, Lice and Scabies, Bruises, Hives, Blisters, lime disease, shingles, Acne, Eczema, Varicella-Zoster Virus Infection, Herpes Zoster, Herpetic Whitlow, Molluscum Contagiosum, Erythema Infectiosum, Plantar Warts, Warts, Rubella, Erythema Multiforme Minor, Hand-Foot-and-Mouth Disease, Verruca Plana, Verruca Vulgaris, Rocky Mountain Spotted Fever, Acne Vulgaris Nodulocystic, Hidradenitis Suppurativa, Furuncle (*S. Aureus*), Rosacea, Folliculitis, Bartonellosis, Folliculitis, Bartonellosis, Impetigo, Transient Neonatal Pustular Melanosis, Miliaria Crystallina, Miliaria Rubra, Scarlet Fever, Pitted Keratolysis, Lepromatous Leprosy, Leishmaniasis, Ringworm, Athlete's Foot, Fungal Nai, *Tinea Versicolor*, Sporotrichosis, Candidiasis (Moniliasis), Yeast Infections, Histoplasmosis, Bedbug Bites, Lyme Disease, Rickettsialpox (Tâche Noire), Bee, Wasp, Hornet, Yellow Jacket Stings, Black Widow Spider Bites, Brown Recluse Spider Bites, Dermatitis From Common Carpet Beetle, Fire Ant Bites, Flea Bites, Body Lice, Jellyfish Envenomation, Contact with Sea Urchin, Syringomas, Lipoma, Desmoplastic Melanoma, Cutaneous Horns, Epidermal Inclusion Cyst (EIC), Skin Tags, Moles, Dermatofibroma, Angiofibroma (Facial), Dysplastic Nevus, Halo Nevus, Congenital Nevomelanocytic Nevus, Dysplastic Nevi (Atypical Moles), Compound Nevus, Spitz Nevus, Epidermal Nevus, Neurofibromatosis (Café au lait), Neurofibromatosis (Crowe's Sign), Neurofibromatosis (Neurofibromas, Sunburn, Solar Keratosis, Poikiloderma of Civatte (POC), Dermatosis Papulosa Nigra (DPN), Addison's Disease, Amiodarone, Melasma, Jaundice, Freckles, Lentigines, Multiple Lentigines Syndrome (Back), Psoriasis Vulgaris Erythematous, Pustular Psoriasis, Erythrodermic Psoriasis, Psoriatic Arthritis, Lichen Planus, Xanthomatosis, Erythema Multiforme, Palmar Pustulosis, Darier's Disease, Poison Ivy, Fixed Drug Eruption, Gianetti-Crosti Syndrome, Iododerma and Bromoderma, Lichen Simplex Chronicus, Sweet's Syndrome, Verrucous Papules, Morphea, Port-Wine Stain, Systemic Lupus Erythematosus, *Livedo Reticularis*, Lymphedema, Hemangioma, Lymphangioma, Dermatomyositis, *Polyarteritis Nodosa*, Erythema Nodosum, Urticaria, Angiokeratoma Circumscriptum, Ataxia-telangiectasia, Cutis Marmorata Telangiectatica Congenita, Henoch-Schonlein Purpura, Kawasaki's Disease, Klippel-Trenaunay-Weber Syndrome, Meningococcemia, Pyogenic Granuloma, Spider Angioma, Necrobiosis Lipoidica Diabeticorum, Vascular Malformations, Cherry Angioma, Peripheral Vascular Disease, anemia, (Fungal Nail Infection), Glaucoma, Cataracts, Age-Related Macular Degeneration, Retinal Detachment, Bacterial Conjunctivitis (Pink Eye), Uveitis, Eye Allergies, Sty (Stye), Keratoconus, Blepharitis, Corneal Ulcer, Diabetic Retinopathy, Strabismus (Crossed Eyes), Floaters, Farsightedness, Nearsightedness, Astigmatism, Genital Warts (HPV), Crabs (Pubic Lice), The Clap (Gonorrhea), Syphilis, Chlamydia, Herpes Simplex Virus Type 1, Herpes Simplex Virus Type 2, Hepatitis B, Chancroid, LGV (Lymphogranuloma Venereum), Canker Sore, and Strep Throat, etc.

Block Diagram

Figure 22:
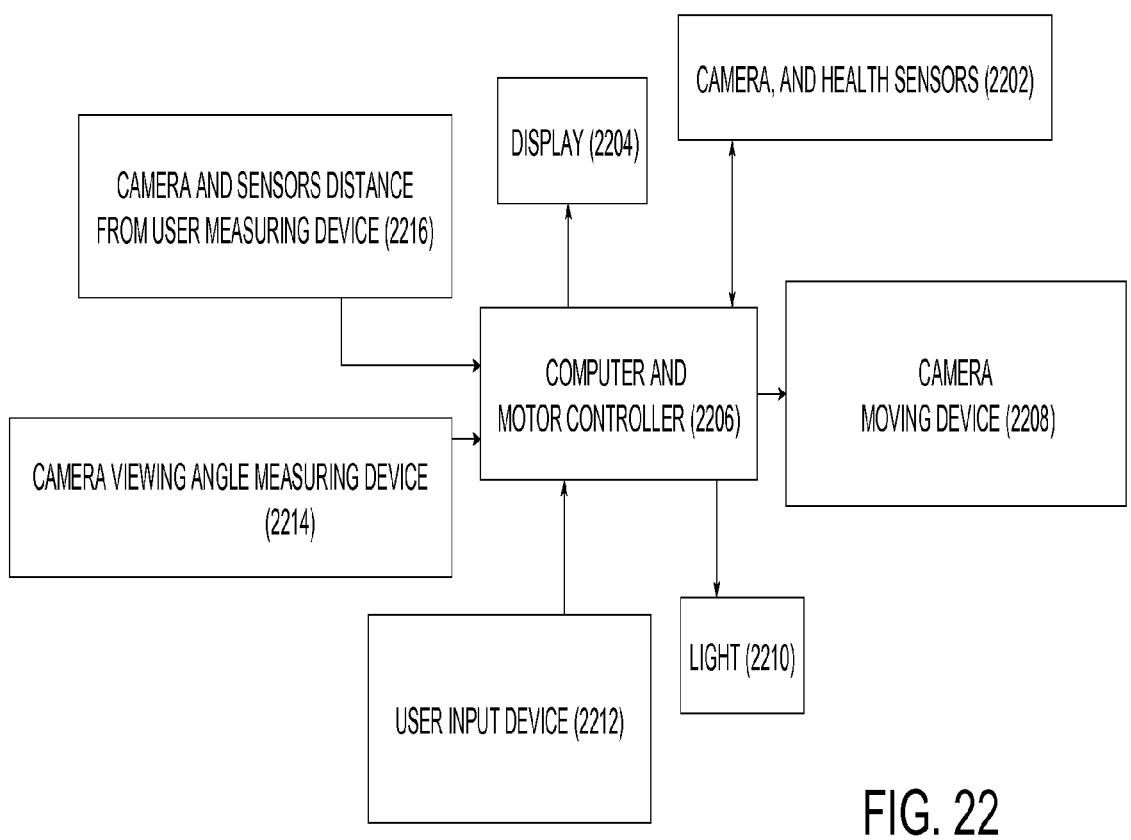
FIG. 22 illustrates a block diagram of hardware connections between components of a movable user health detecting camera, and health sensors.

FIG. 22 illustrates a block diagram of some of the hardware components connections of the device, cameras and health sensors (2202), display (2204), computer and motor controller (2206), camera moving device (2208), light (2210), user input device (2212), camera viewing angle measuring device (2214), camera and sensors distance from user measuring device (2216).

Two Camera Moving Devices Health Testing a User's Back Operation

The user is able to view their back and sides on the display, while occupying the toilet seat. The user can choose to manually move the camera to view their back, or have the computer automatically move the camera to view their back. The user can choose either a manual or automatic moving of health sensors from options, on the menu shown on the display.

Visual Computer Diagnosis of the Body

Figure 7:
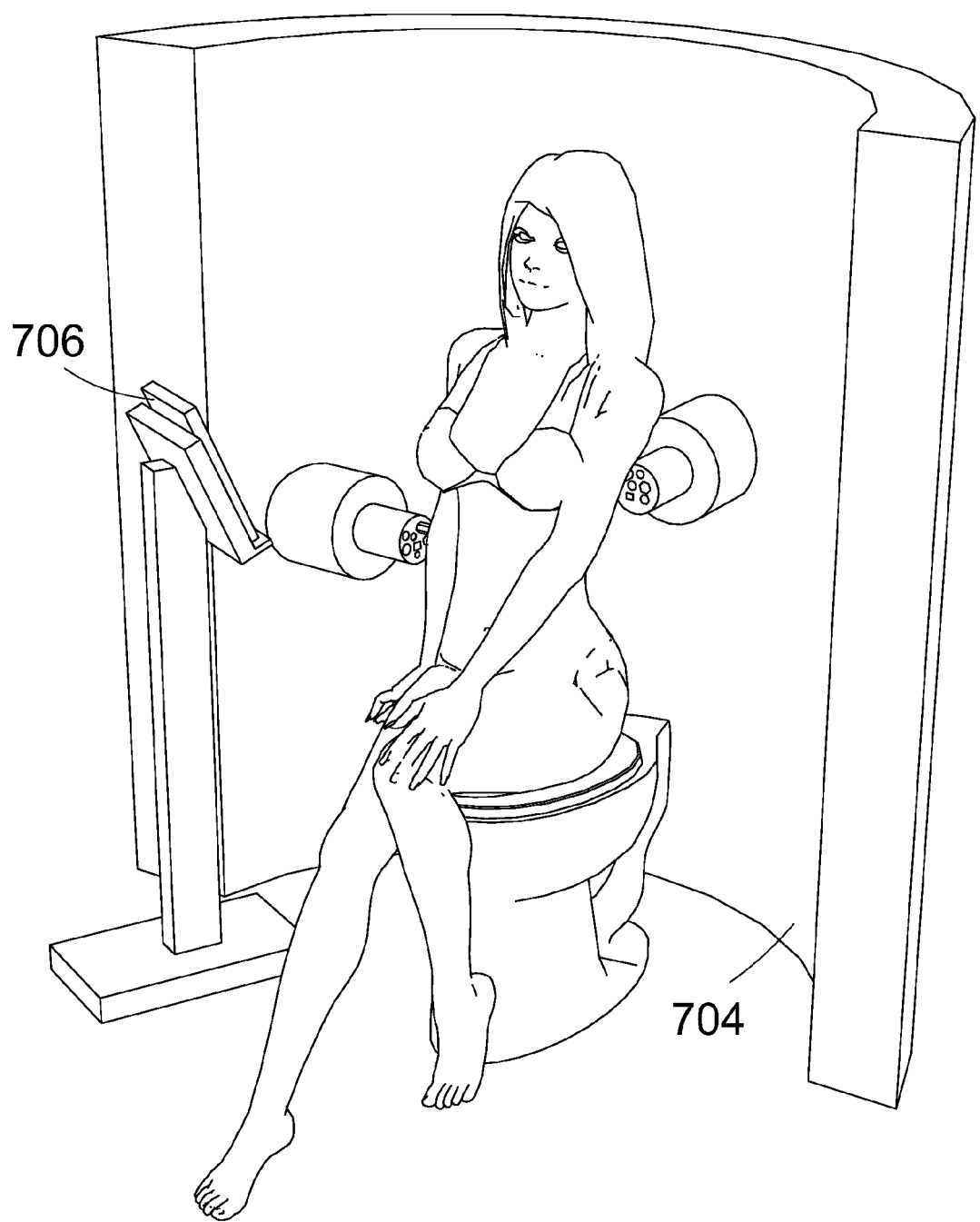
FIG. 7 shows a perspective view of a curved wall encompassing a toilet's back and sides, with two camera moving devices attached to the curved wall, each camera moving device having a camera and health sensors incorporated into to them.

The camera's 702 views the user's body, as shown in FIG. 7. The computer looks for visual objects on the body which are outside of a pre-programmed default healthy body skin view. When the computer finds different object's on the body, it searches its data bases to identify the different object. The computer searches for matches of the views of the object, with visual body problems stored in a computer data base of body object problems, such as, skin cancer and other ailments. On the internet the computer also searches a data base of visual body problems. The computer uses body disease recognition software to identify body object problems. The visual image of the body object is turned into a two 2D or 3D mathematical algorithm. The body 2D or 3D mathematical algorithm, is compared a to data base 2D or 3D mathematical algorithm in the ailments data bases, to find a match between the algorithms. When a match is found the body algorithm is identified.

The VisualDx software aids in the identification of dermatologic, infectious, genetic, metabolic, and nutritional and occupational diseases, benign and malignant growths, drug-induced conditions, and other injuries. The VisualDx system allows the computer to search by diagnosis, build a patient-specific differential, or look up drug-induced adverse reactions by medication.

The computer can also connect to visual diagnosis websites on the internet, which have visual data bases on the cloud, to automatically visually diagnosis the viewed body. The cloud based computers diagnosis, visual images of the user's body, which are sent to them.

Sensors and the video camera 702 move over the user's back, as show in FIGS. 7 and 8. The sensors view and or contact skin on the user's back. The sensors detect and analyses different health measurements of the user. The sensors and camera detect possible health concerns. The tablet computer 706 acts as a remote control display, which visually shows the sensor measurements, and possible health concerns.

Display Operation

The user's uses their input into eye tracking sensor, to direct the movement of camera moving device and the camera. The display shows the camera's view of the user back. The cursor is shown in the center of the camera's view. The camera's center of view the camera follows the cursor. The moving device moves the camera to keep the camera's view centered on the shown cursor. The user eye inputs a location on the display of the shown back, away from the center of the camera view, the moving device 704 will move its center view to the location. When the camera reaches the cursor's off center location the camera's movement will stop, this location will be centered in the display.

The cursor can be deactivated or move out of the center of the screen to see what's shown underneath the cursor, or in the center of the screen. The cursor can be shaped like a circle, and the circle can be enlarged to have a better view of the camera's center view. The cursor's shape can be different shapes.

The user moves the camera over their back, by eye inputting the location and a path shown on the user's body that they want the camera to view and follow. The camera's view is shown on the display as it moves over the back, and shows the view when stationary. The camera views the users back, and displays views of the user's back as the camera's view moves over the user's back.

The camera will follow a line or path drawn on the user's body, viewing and showing the view as the camera follows the line. The user can activate the path following of the moving device, and draw the electronic line on their shown body. The user uses their eye movements, to draw the line with the cursor. A 3D Hololens headset display can also be connected to the computer, and used by the user, to input in the computer.

Heath Care Providers Remotely Viewing

Health tests and camera viewing of the user can be performed by heath care providers, remotely at a location outside of the toilet area. The providers view a remote display which shows the same information as shown on the user's display. The providers can perform health tests on the user. This enable the providers to preform health tests on users who may be health challenged. The providers can also monitor health tests carried out by the user. The remote display shows the user's heath information, and the camera's view of the user.

Health Test Sensors

The user sits on the toilet seat. The user views a menu of health tests on the display screen. The user's eye movements activate the icon that is associated with the health test they want to activate. The health test is activated. A health sensor associated to the heath test, tests the user's body. The heath test information is sent from the health sensor, and received by the computer. The computer analyses the body information, with health test information analyzing software. The computer finishes the analysis of the information. The analyzed results are displayed on the display. The user views the health test results. If the results have possible health concerns, the user may discuss the results, with health care professionals. The computer can automatically send, over an internet, health problem data to health care providers for analyses.

The user can activate more than one health test at a time, and view the results. The user can pre-set a group of health test that they can be user activated. The computer can automatically run pre-set health tests, when a user is detected, sitting on the toilet seat, and display the test results.

The camera moving device moves the sensors to contact the user's skin. The cancer detecting laser analyses the user's body back and side areas. The camera moving device 704 moves the cancer cell detecting light 730 to contact the user's skin.

The glucose sensor 732, is positioned to view the user's back skin as they sit on the seat. The user's blood sugar is measured by directing the specialized laser at the user's skin. The laser passes through the skin cells, without causing damage, and is partially absorbed by the sugar molecules in the patient's body. The device 104 uses the amount of laser light absorption, to measure the level of blood sugar in the user's blood. The device uses a 'quantum cascade laser' to produce mid-infrared light. The system uses infrared laser light, which is just beyond the spectrum light visible to the human eye The Raman spectroscopy device 722, optically views the user's skin to biochemically analyze the skin. The blood pressure sensor 734 measures a user's blood pressure by contact with their skin. The moving device presses the blood pressures sensors against the user's skin until the test is complete, then withdraws the sensor from the user's skin. The blood pressure sensor contacts a user's skin when they sit on the toilet seat. The blood pressure sensor detects the user's blood pressure while they sit on the toilet seat.

The Malaria detector is moved by the moving device to a vein in the user's wrist. The malaria detector is pressed against the user's vein. The vein is visually detected by the user or computer.

The Malaria detector 738 works by pulsing energy into a vein in a person's wrist or earlobe. The laser's wavelength doesn't harm human tissue, but is absorbed by hemozoin waste crystals that are produced by the malaria parasite *Plasmodium falciparum* when it feeds on blood. When the crystals absorb this energy, they warm the surrounding blood plasma, making it bubble. An oscilloscope placed on the skin alongside the laser senses these nanoscale bubbles when they start popping, detecting malaria infections in only 20 seconds.

The skin temperature sensor 762 is used to measure skin temperature. The temperature sensor views the user's skin, when moved in range by the camera moving device. The temperature can be used to detect fever and high fever temperature.

Display

The display is viewable by the user. The display screen is in view of the user. The display screen displays user health information sent to the display by the computer. The computer analyzes the user's health data. The computer updates the user on the user's health condition, and detected health problems. The computer alters the user to blood glucose level, blood pressure, etc. The computer alters the user, to their blood sugar level or other health concerns, by displaying, a visual health message on the display screen that the user can view Facial recognition software, is used with a camera on the tablet. The facial recognition, is used to identify the user. The camera images the user's face, as the user positions the camera tablet to view their face. The facial image, is compared, by the computer, with stored images of users, to find a match with the stored images. When a match with the viewed user image, and the stored image is found, the viewed user is identified. The identified user is associated with their stored profile. The stored profile contains health information about the user. The health information can be inputted by the user, and information collected from health sensor tests.

The identified user is associated with the user's preprogrammed user profile, containing, the user's age, gender, and height, etc. The user's profile is used to store collected health data, associated to the user. The stored data, can be used to detect changes in the data, which are of a health interest.

Camera Moving Device Moving Health Test Sensors and Camera

The two camera moving devices operate simultaneously, performing two health test at the same time. The moving devices 704 extends outward, from the back moving plane 704. The camera distance sensor detects the camera's distance to the user. If the user moves forward or back ward the moving device moves with the user, and will extend or retract synchronously with the user's movements. If the user moves faster than the moving device, and the user contacts the moving device, the device is flexible, and exerts minimal contact pressure on the user. The moving device's flexibility avoids hard contact with the user should the user move backward expectantly.

The cancer detecting light sensor face 730 with the sensor can tilt up and down, and left and right to maintain a perpendicular view of the user's back. The tilting allow the sensors face to contact the back in a parallel position to the back. The computer controls the sensor movements, to a desired location on the back. The user can controls the sensor movements, to a desired location on the back, by eye movement inputting into the tablet remote control.

The sensor face 730 with sensors can extended to the user's back, or retract away from the back. The sensors can extend out ward from the face of the sensor moving device, and retract into the face. The extension and retraction of sensors allows sensors to contact the user's skin more efficiently, and or to possibly have a better view of the user's skin.

The sensor and moving device moves on the curved moving plane. The moving device is moved by bands which are connected to the moving device which moves the device on the x and y axis of the plane. A motor powers the moving device which moves bands attached to the moving device. The bands move up and down, and right and left which moves the camera device in those directions. The computer instructs the moving device, to move the camera to locations on the moving device plane.

The camera and sensors, moves on the plane parallel to a user's back while perpendicular or at a 90 degree viewing angle of the user's back, as shown in FIG. 7. The camera can move to any location on the curved plane, to view the back. The camera moving device is connected to the computer.

Laser Used to Detect the Camera's Angle from the Body

The camera adjusts the cameras viewing angle as it moves over the back, to maintain a perpendicular viewing angle of a back area. The camera's viewing angle changes as it view moves over the changing angles of the users back. The laser angle measuring device, measures the cameras viewing angle to an area on the back. The computer moves the cameras angle to maintain a perpendicular view of the area. The computer is programmed with software to detect the lasers angle. The camera and computer programmed with software that allows the computer to measure the distance to the user's back using the camera view.

The laser distance measuring device 754, and angle measuring device 754 is used to measure the sensors face in relation to the user's back, and the angle of the face to the user's back. The laser device is connected to the computer. The software allows the camera to measure its viewing angle to the back.

The camera and laser, senses angle and distance information, which allows the computer to keep the face, at the best angle and best distance to the users back, for the sensor being used. If the user moves, the computer adjusts the cameras view to the new back position.

Laser Used to Detect the Camera's Distance from the Body

A laser ranger finder 754 distance measuring device is used to measure the camera's distance to the user's back. The laser also measures the cameras viewing angle 754, in relationship to the viewed area of the body. The same laser is used for measuring distance and camera viewing angle.

The laser distance measuring software is used with the laser, to maintain an optimal camera viewing distance from the back, while the camera is moving along the posterior, and while stationary at positions on the posterior. The camera can refocus if the camera's viewing distance increases or decreases from the skin.

The camera's viewing distance changes, due to the curves of the back, and the backs incline while the user is sitting on the seat. The moving device keeps the cameras distance from the back the same, as it moves over the back. The camera's focus and zoom will change as the distance from the back changes maintaining a clear view of the back.

The computer zooms the camera's lens in and out, to maintain a constant sized visual viewing area, of the viewed back area, as the viewing area moves over the back The zooming allows the viewed details on the user's back stay the same size on the display, as the back's distance from the camera changes, as the camera views different areas of the back.

An ultrasonic measuring sensor 752 is also used to detect the cameras distance from the user's body, and is connected to the computer, and attached to the moving device.

Software Flowchart of Operation

Figure 23:
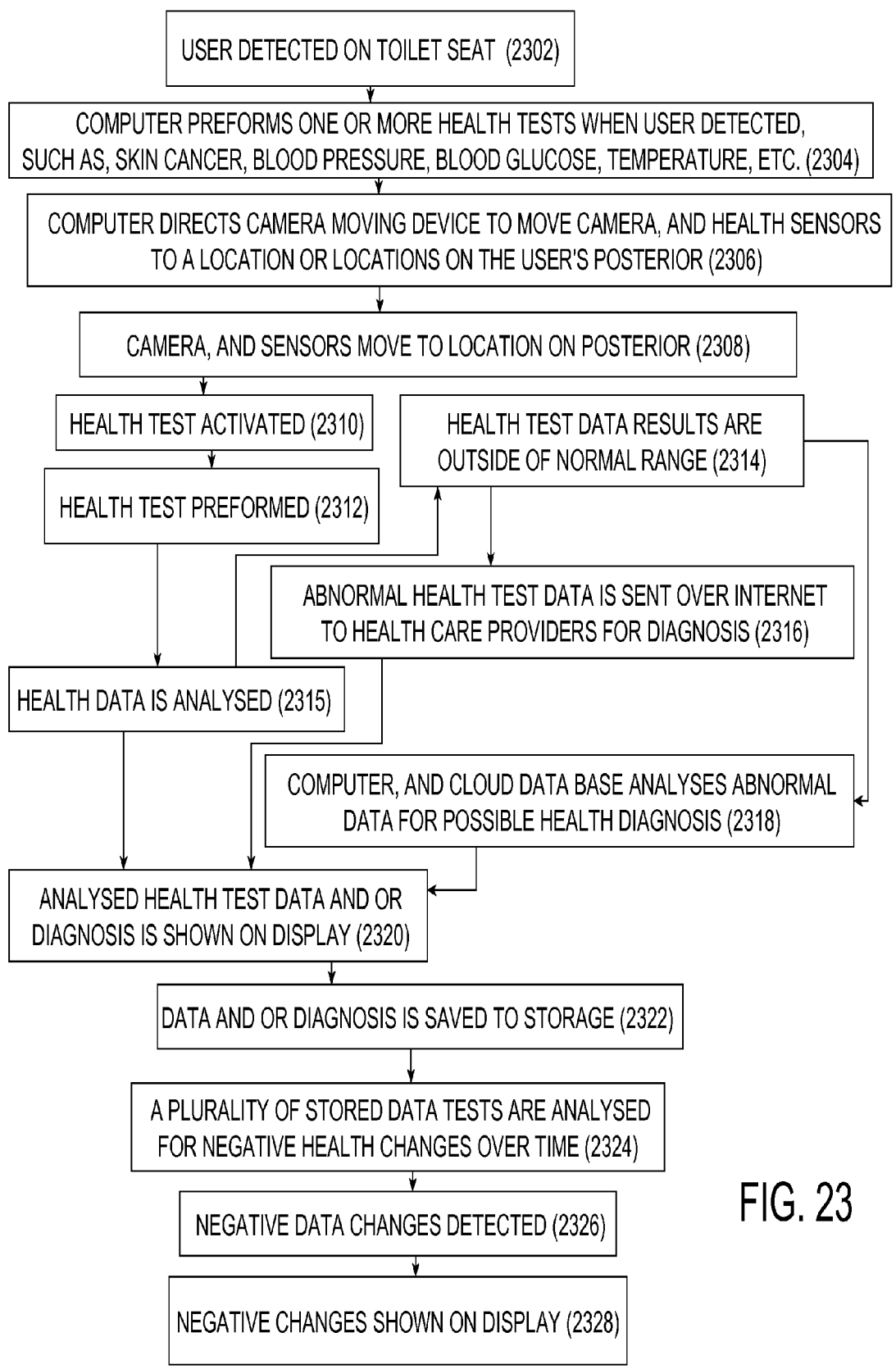
FIG. 23 depicts a software flowchart of a movable user health detecting camera, and health sensors.

FIG. 23 shows software steps of the operation of the health sensors, user detected on toilet seat (2302), computer to preforms one or more health tests when user detected, such as, skin cancer, blood pressure, blood glucose, temperature, etc. (2304), computer directs camera moving device to move camera, and health sensors to a location or locations on the user's posterior (2306), camera, and sensors move to location on posterior (2308), health test activated (2310), health test preformed (2312), health test data results are outside of normal range (2314), health data is analysed (2315), abnormal health test data is sent over internet to health care providers for diagnosis (2316), computer, and cloud data base analyses abnormal data for possible health diagnosis (2318), analysed health test data and or diagnosis is shown on display (2320), data and or diagnosis is saved to storage (2322), a plurality of stored data tests are analysed for negative health changes over time (2324), negative data changes detected (2326), negative changes shown on display (2328).

A Health Sensing Toilet Seat Description

Figure 10:
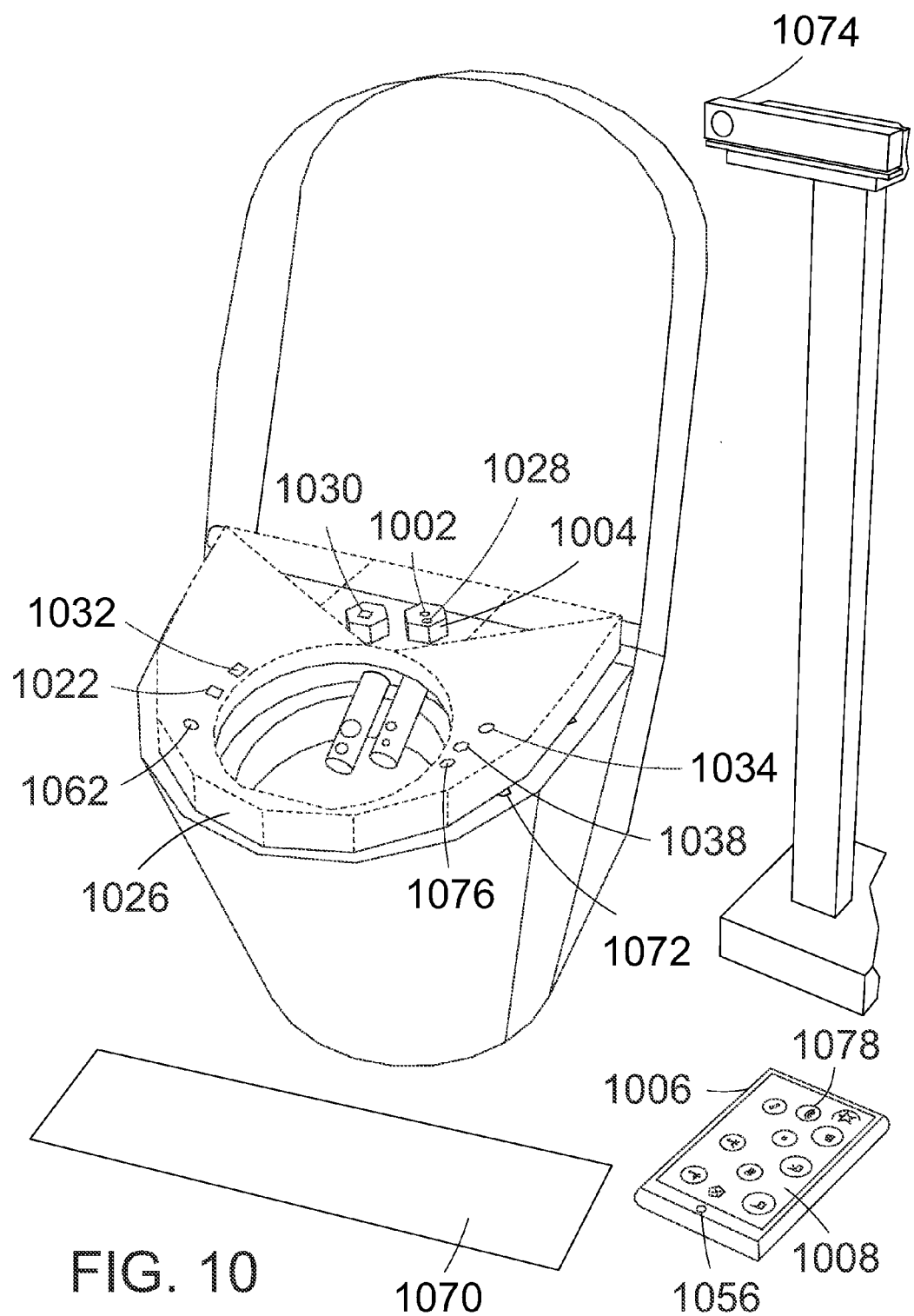
FIG. 10 shows a perspective view of a toilet seat with attached cameras and health sensors, a weight scale, a Kinect camera, and a tablet computer.

Health sensors are positioned on a toilet seat. The sensors contact a user's body when they are on the toilet seat, as shown in FIG. 10. The toilet seat 1026 top is a clear glass window.

Health Sensors

A cancer cell detecting laser 1030 is, is attached to the camera the moving device 1004, and connected to a computer 1006. An electrocardiogram (ECG or EKG) monitor 1022, is attached to the toilet seat, and connected to the computer. A blood pressure sensor 1034 is attached to the top of the toilet seat, and connected to the computer. A skin temperature sensor 1062 is, attached to the top of the toilet seat, and connected to the computer seat.

A blood glucose sensor detecting laser 1032, is attached to the toilet seat 1026, and connected to the computer 1006. The laser blood sugar sensor is incorporated into the toilet seat.

A Cambord Pico camera 1002 is attached to a camera the moving device, and connects to the computer. Intel real sense software attached to the camera moving device. The computer is connected to a motor controller (not shown). The motor controller is connected, to the health sensors and the health cameras. The computer is connected, to the health sensors.

The toilet seat 102 has two weight scales, one to measure the user's weight on the toilet seat. The toilet seat scale has four weight sensors 1072 that support the toilet seat when it in the occupied position. The four sensors 1072 measure the weight of the user on the toilet seat. A second foot weight scale 1070 is connected to a foot rest scale 1070, and measures the weight of the user's feet on the foot rest scale as shown in FIG. 10. The two seat and foot scales are connected to the computer. The computer combines the seat weight measurement and the feet weight measurement. The combined weights result in the user's full body weight.

A Kinect camera 1074 is connected to the computer, and can view the user's skin for signs of skin cancer. Other cameras can connected to the computer.

Electrical impedance sensors 1076, are attached to the top of the toilet seat, and connected to the computer. The sensor 1076 sends a harmless tiny electrical current from one thigh to the other thigh. The electrical current measures electrical impedance of the electrical current through the user's body.

A heart rate monitor 1038, and blood oxygen saturation monitor is attached to the toilet seat. The monitor's sensor is exposed on the top of the toilet seat surface, to the user's skin.

The computer is a tablet computer. The computer connects to and has an Intel realsense camera. The computer is programmed with Intel realsense software 1302.

A Health Sensing Toilet Seat Operation

The toilet seat with heath sensors, uses passive interaction with a user to diagnosis their body's health. The health sensing toilet seat, diagnosis the user's health, with cameras and sensors, while they are sitting on the toilet seat, as shown in FIG. 10.

The user sits on the toilet seat 1026. A sensor detects the user on the toilet seat. The detection of the user, activates the sensors and camera. Health tests are done automatically by sensors and cameras. Health test can also can be set, to be activated manually by the user.

The user views a menu of health tests, on the display screen. The user touch freely inputs into the computer, by mid-air hand gesturing in front of the mid-air hand gesture camera 1056. The input controls a cursor, etc., shown on the display. The user's mid-air touch activates an icon that is associated with the health test they want to activate. The health test is activated, and tests the user's body. The heath information is received by the computer. The computer analyses the health information, with health test information analyzing software. The computer finishes the analyzing the information. The analyzed results, are displayed on the display. The user views the health test results. If the results have possible health concerns, the user may discuss the results, with health care professionals.

The camera has a light 1028 the illuminates the posterior, when the camera is viewing the posterior. The toilet seat window is clear which allows the camera, sensors and lasers, to view the skin that contacts the toilet seat top.

The health sensors and the camera 1002 move under the user's posterior, inside the clear toilet seat, as show in FIG. 10. The camera moves inside the toilet seat, and views the user's skin pressed against a window on the top of the seat. The top of the seat is clear glass. The camera detects the angle of the viewing glass to the camera lenses. The computer uses the angle information to move the camera viewing angle, to keep the viewing angle perpendicular, directly on the user's skin. The toilet seat is attached to a toilet.

The moving device moves the camera 1002 and skin cancer detecting laser 1030, move inside the toilet seat. The plane that the camera and laser move on is parallel, to the toilet set curvature, which keeps the camera and laser view of the user's skin perpendicular.

Sensors also contact the posterior and or leg skin, when the user sits on top of the sensors on the seat. A remote control computer display 1008 visually shows the sensor measurements, a view of the posterior, and possible health concerns.

The laser blood sugar sensor contacts the user's skin. The glucose sensor 1032, is positioned to view the user's skin as they sit on the seat, and their skin contacts window, and allows the sensor laser beam to contract the user's skin. The body temperature sensor 1062 contacts the user's skin, and is used to measure skin temperature. The temperature can be used to detect fever and high fever temperature. A female user's temperature can be used to determine the time that they are ovulating.

The user's weight is measured by the toilet weight scales 1070, 1072. The user's weight is displayed 1078 on the display 1008. The user can see their weight on the display. The users displayed weight may be beneficial in aiding weight loss in the user. Seeing their weight, on a regular basis may aid the user in improving the management of their weight. The scales can measure the user's weight, before and after they eliminate, to calculate to weight of their elimination. The scale can measure the user's fecal output. The weight of the elimination can be displayed. The amount of the user's elimination may aide in monitoring the user's health.

The toilet scales remove the need for the user to weigh themselves while standing on a separate scale. The seat scale eliminates the possibility of a user falling off of a standing scale while weighting themselves. For users with body weight issues the regular weight information, may aid in increasing their awareness of the body.

A Kinect camera 1074 is located on the toilet, and can visually monitor a user skin for signs of skin cancer. The user's body is viewed for skin cancer and other ailments, as they move around the bathroom. A nude user in the bath room, or entering the shower, may have a full body skin cancer view or scan by the Kinect. The computer keeps a record, of the of the user's visual body scans. The scans are be analyzed for changes in coloration, or growth of the skin, etc. Other cameras can be used to view the user.

The user's fat mass is measured by the electrical body impedance device 1076. By analysing the user's body electrical impedance the computer can infer body fat percentage of the user, etc. The Seca impedance device 1076 breaks down weight into several compartments which are highly relevant in medical care, namely, fat mass and fat-free mass, total body water, extracellular water, skeletal muscle mass and lean soft tissue. The user inputs their body height, age, and gender, in to the computer test.

The heart rate, and blood oxygen sensor 1038 measure the user's heart rate, and blood oxygen saturation level. The heart monitor could also be the Kinect sensor 1074 which measure the user's heart rate by viewing the user's body. A visual heart rate monitor can be used which detects the movement of the head each time the heart contracts and expands. A heart rate monitor detecting raw pulse waveform, can also be used to detect irregular heart rate, and provide an early warning of heart problems.

The electrocardiogram sensor 1022 measure the user's EKG. The electrocardiogram (ECG or EKG) is a test that checks how your heart is functioning by measuring the electrical activity of the heart. The blood pressure sensor 1034, contacts the user's body when they are on the seat, and measures the user's blood pressure.

The sensor measures the user's EKG. The electrocardiogram (ECG or EKG) sensor 722 checks how the user's heart is functioning by measuring the electrical activity of the heart. With each heartbeat, an electrical impulse (or wave) travels through your heart. This wave causes the muscle to squeeze and pump blood from the heart. An ECG measures and records the electrical activity that passes through the heart. A health care provider can determine if this electrical activity is normal or irregular. An ECG may be recommended if user is experiencing arrhythmia, chest pain, or palpitations and an abnormal ECG result can be a signal of a number of different heart conditions The EKG sensor detects abnormal heart rhythms that may have caused blood clots to form. Detectable heart problems, include a recent or ongoing heart attack, abnormal heart rhythms (arrhythmias), coronary artery blockage, areas of damaged heart muscle (from a prior heart attack), enlargement of the heart, and inflammation of the sac surrounding the heart (pericarditis). Detect non-heart conditions such as electrolyte imbalances and lung diseases. Monitor recovery from a heart attack, progression of heart disease, or the effectiveness of certain heart medications or a pacemaker.

Full Viewing and Health Sensing of a User's Body Description

Figure 11:
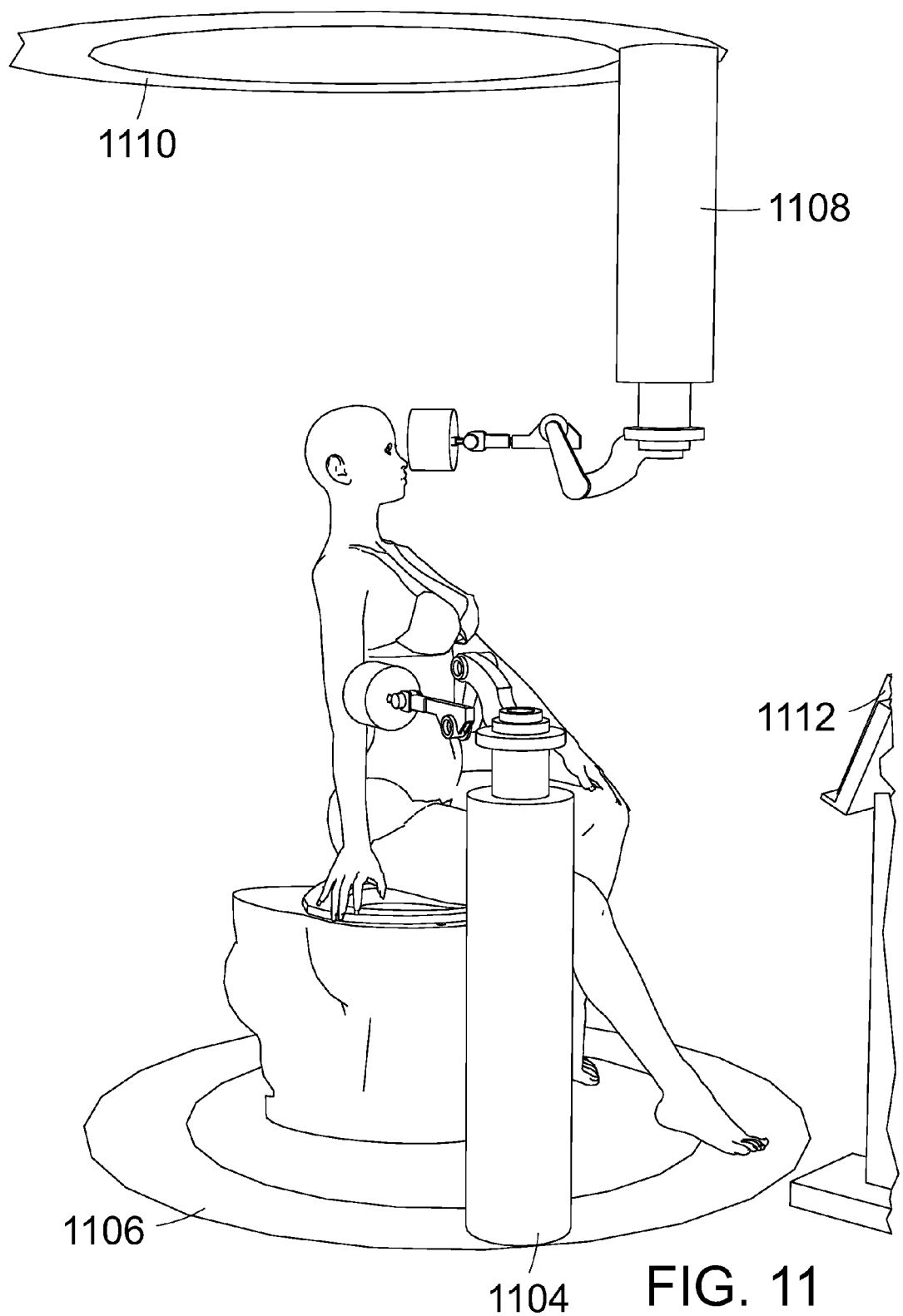
FIG. 11 shows a perspective view of a two camera moving devices on circular tracks, a toilet, and a tablet computer.

Health sensors and cameras are used to view the user, and sense the user's health, as shown in FIG. 11. A camera moving device 1104, is attached to a circular track 1108 on a floor, and a second camera moving device 1106 is attached to a circular track 1110 on a ceiling, located around a user when they are sitting on a toilet.

Eye identification software to find the eye's location is programmed in to the computer. Eye examination software is programmed into a computer 1112. Eye disease recognition software is programmed in to the computer. The tablet computer is viewable by the user. Facial and mouth recognition software is programmed into the computer. Visual oral mouth health sensing software is programmed into the computer.

Full Viewing and Health Sensing of a User's Body Operation

The moving device 1104, moves on a circular track on a floor 1108, around the user when they are sitting on a toilet, as shown in FIG. 11. The second moving device 1106, moves on a circular track 1110 on a ceiling, around the user when they are sitting on the toilet. The circular track allow the camera and camera, and health sensors to contact the user's body from 360 degrees.

For safety the moving device stops and turns off if it contacts, the user or meets any resistance while moving. The user can keep their feet off of the track while the camera is viewing them.

The user preforms the eye test manually by activating the eye test on a displayed menu. The user can then manually move the camera to their eye location, or have the computer automatically move the camera to the user's eyes. The computer uses eye identifying software to detect the location of the user's eyes. When the eyes are located the computer move the camera to within 15 cm to view the user's eyes. The camera can move closer to the user's eye if needed. A displayed sign asks the user to look into the camera's lens. The sign text is also audibly broach cast by the computer, buy using text to speech software. The eye test is performed when the computer detects the user looking into the camera lens. The eye results are displayed on the display. The computer searches for matches of the views of the eyes, with visual eye problems stored in a computer data base of eye problems. The computer 1112 uses eye disease recognition software to identify eye problems.

The ceiling camera's extends from ceiling. The camera views the user's eyes and checks for Glaucoma, Cataracts, Age-Related Macular Degeneration, Retinal Detachment, Bacterial Conjunctivitis (Pink Eye), Uveitis, Eye Allergies, Sty (Stye), Keratoconus, Blepharitis, Corneal Ulcer, Diabetic Retinopathy, Strabismus (Crossed Eyes), Floaters, Farsightedness, Nearsightedness, and Astigmatism.

The camera can view the inside of the user's mouth. The computer audible asks the user to open their mouth. The user opens their mouth, and the cameras views the inside of their mouth. The light illuminates the inside of the mouth. Health ailments are searched for inside mouth, such as, sore throat, oral cancer, and tongue diseases, etc.

Back Viewing Stationary Cameras on the Bottom of a Toilet Seat Lid Description

Figure 19:
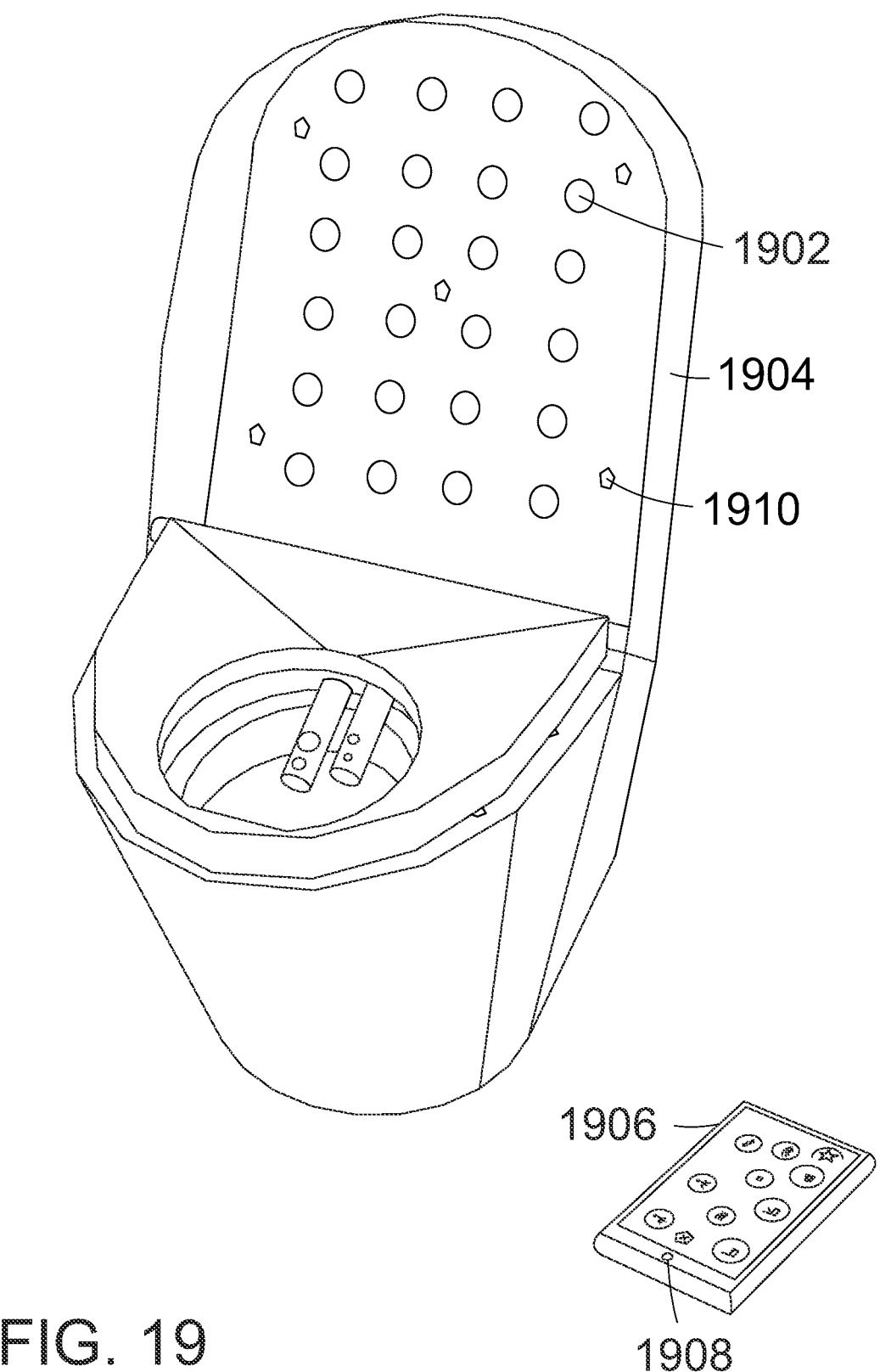
FIG. 19 shows a perspective view of cameras, and imaging lasers attached to the bottom on a toilet seat lid, and a tablet computer.

Cameras 1902 are attached to the bottom of a toilet seat lid 1904, shown in FIG. 19. The lid is expandable. The cameras are connected to a tablet computer. The computer is inside of a protective clear housing (not shown). The computer has a display. The display is viewable buy a user. The tablet has a microphone 1908.

Video stitching software is programmed into the computer. Visual skin cancer melanoma, automatic diagnosis detecting software is programmed into the computer. Skin diagnosis software is programmed in to the computer, for diagnosing, of health conditions, such as, pressure sores, bed sores, herpes, psoriasis, and skin cancer, etc.

The computer is programmed with a computer operating software. The computer is programmed with a camera operating software. Light emitting diodes LED lights 1910 are attached to the bottom of lid. Skin cancer illuminating lights (not shown), are attached to the bottom of a toilet seat lid.

The computer is programmed with a user health alert software, for alerting the user of health problems. The computer is connected to an internet. The computer is programmed with a software for communicating with health care providers over the internet about health problems viewed by the cameras, and diagnosed by the user, and or computer.

A software for creating a user profile is programmed into the computer 1906. A software for associating the user with imaging data, and heath diagnosis data is programmed into the computer, for analysing and detecting positive and negative health changes of the user.

The input device is the microphone. User voice recognition is used for inputting voice commands into the computer. Voice recognition software is programmed into the computer. The input allows the user to operate the devices, display view, cameras without touching the display. The touch free user input device is connected to the computer.

Cameras can also be attached to the back of a toilet, or the front of a toilet tank. When the lid is moved to the upright position, the lids cameras are flush with the cameras on the back of the toilet. The lid is held in a horizontal position by a magnet in the lid and a magnet in back of the toilet.

Cameras can also be attached to the front of a toilet bowel, to view the back of the user's legs. Cameras can be inside a clear toilet seat, to view the legs and posterior of the user. Cameras can be attached to a ceiling to view the lap, shoulders, and head of the user. Cameras can be attached to the inside of a toilet bowel, to view the posterior of the user.

Back Viewing Stationary Cameras on the Bottom of a Toilet Seat Lid Operation

The cameras 1902 view a user's back, when they are seated on a toilet seat, shown in FIG. 19. The view of the user's body is shown on the display. The video stitching software is used to combine the different camera's view of the user's body. The software stitches the together different views, to create one continuous view of the body. The body can be viewed from different perspectives on the screen, with a perpendicular view of a viewed area of the body is a default view of the user. The views perspective can be changed by the user.

The computer 1906 receives the views of the user's and analyses the user images for problems, such as, skin cancer, and other ailments. If a problem is found on the user's body, an alert is shown on the display, with the problem describe in writing, a picture of the problem is displayed. An audio alert vocalizes the displayed writing of the problem, using a speaker, and using text to voice translation software.

When the lid is lifted into the up position, the lid expands vertically to 1.6 times its size when it is in a horizontal position. The expansion of the lid allows the camera to view the users complete back.

Full Body Viewing of a User on a Toilet by Stationary Cameras Description

Figure 12:
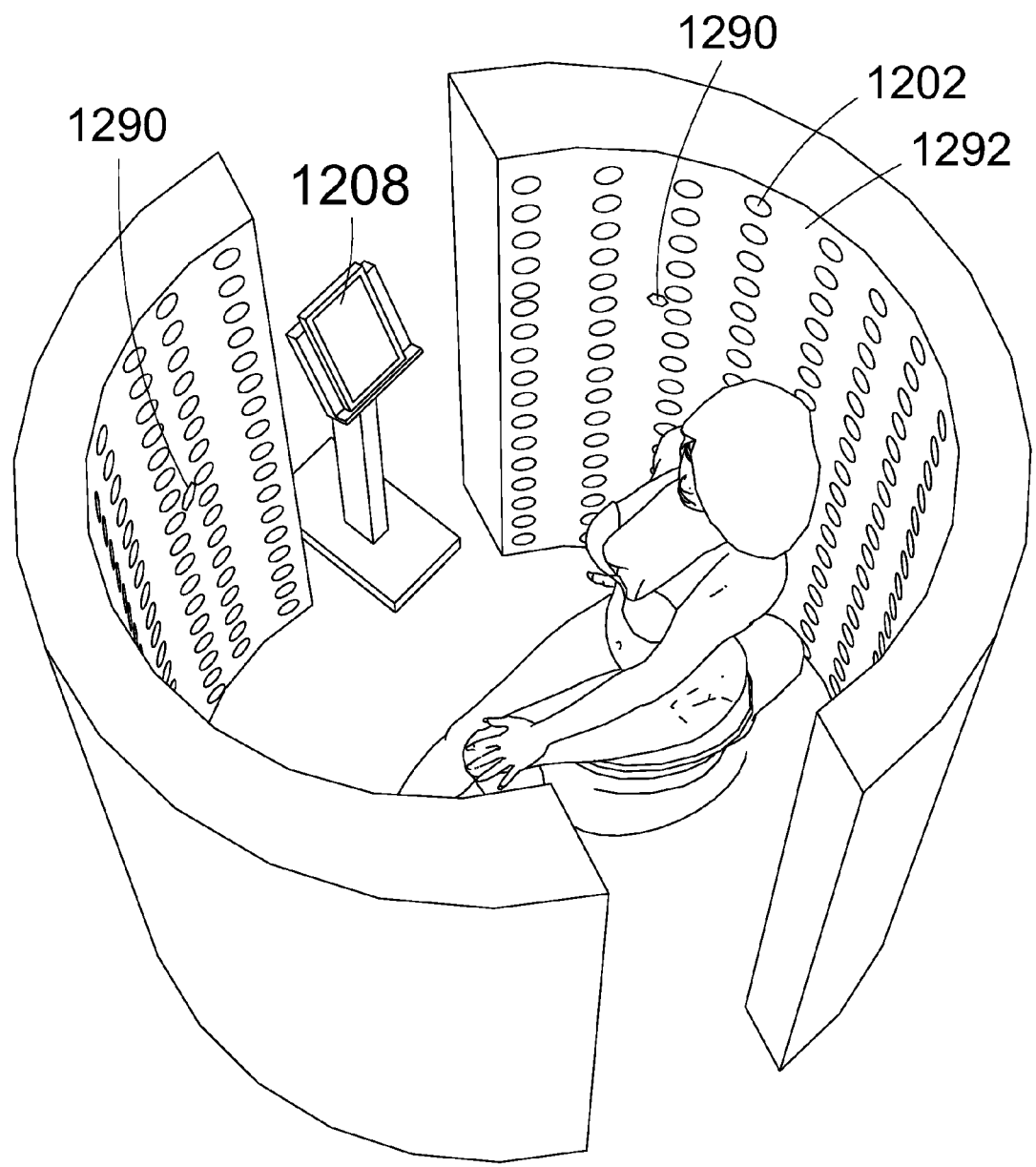
FIG. 12 shows a perspective view of stationary cameras, and 3D imaging lasers attached to a semi-circular wall surrounding a toilet, and a tablet computer.

High definition cameras 1202 are attached to a camera attaching device 1292, as shown in FIG. 12. The cameras are connected to a computer. Cameras can also be used inside the toilet bowel to view the user's posterior. Cameras can be inside the toilet seat to view the user's legs and posterior contacting and near the toilet seat. The back of the user's legs can be viewed to by cameras attached to the front of the toilet. The front of the user's body is viewed by cameras placed in front of the user's facing the user, viewing the user's front. The user's lap and top of their body is viewed by cameras on a ceiling (not shown) above the user.

3D Imaging Lasers

Four three dimensional 3D Lasers 1290 are attached to the camera attaching device, surrounding the users body. The lasers are connected to the computer. The computer is programmed with a laser 3D user image creating software.

The lasers are made by the Human Solutions and TC companies. Polyworks body imaging software is programmed into the computer. Kinect body scanners made by the Microsoft company, or body scanners made by the Artec company can also be used to scan the user's body. The user's eyes are safe in the presence of the lasers. The Lasers for 3d body imaging, are used weight loss detecting and viewing the body in 3D.

Full Body Viewing of a User on a Toilet by Stationary Cameras Operation

The cameras 1202 view the user's skin on their body, when they are seated on the toilet seat, as shown in FIG. 12. The computer receives the views of the user's and analyses the user images for problems, such as, skin cancer. If a problem is found an alert is shown on the display 1208, with the problem describe in writing, a picture of the problem is displayed, and the alert is audio specking the problem, with text to voice translation and broadcast of the shown text.

3D Imaging Lasers

The lasers and cameras 3D image the user while they are sitting on the toilet. The lasers and cameras view of the user's body is sent to the computer. From the received views the computer creates a 3D view of the user's body. The view is stored in the computer for comparison to other 3D views of the user's body. The comparison of the views is used to check for changes in shape of the user, such as weight gain or weight loss.

Standing Full Body Scan by Stationary Cameras. Description

Figure 13:
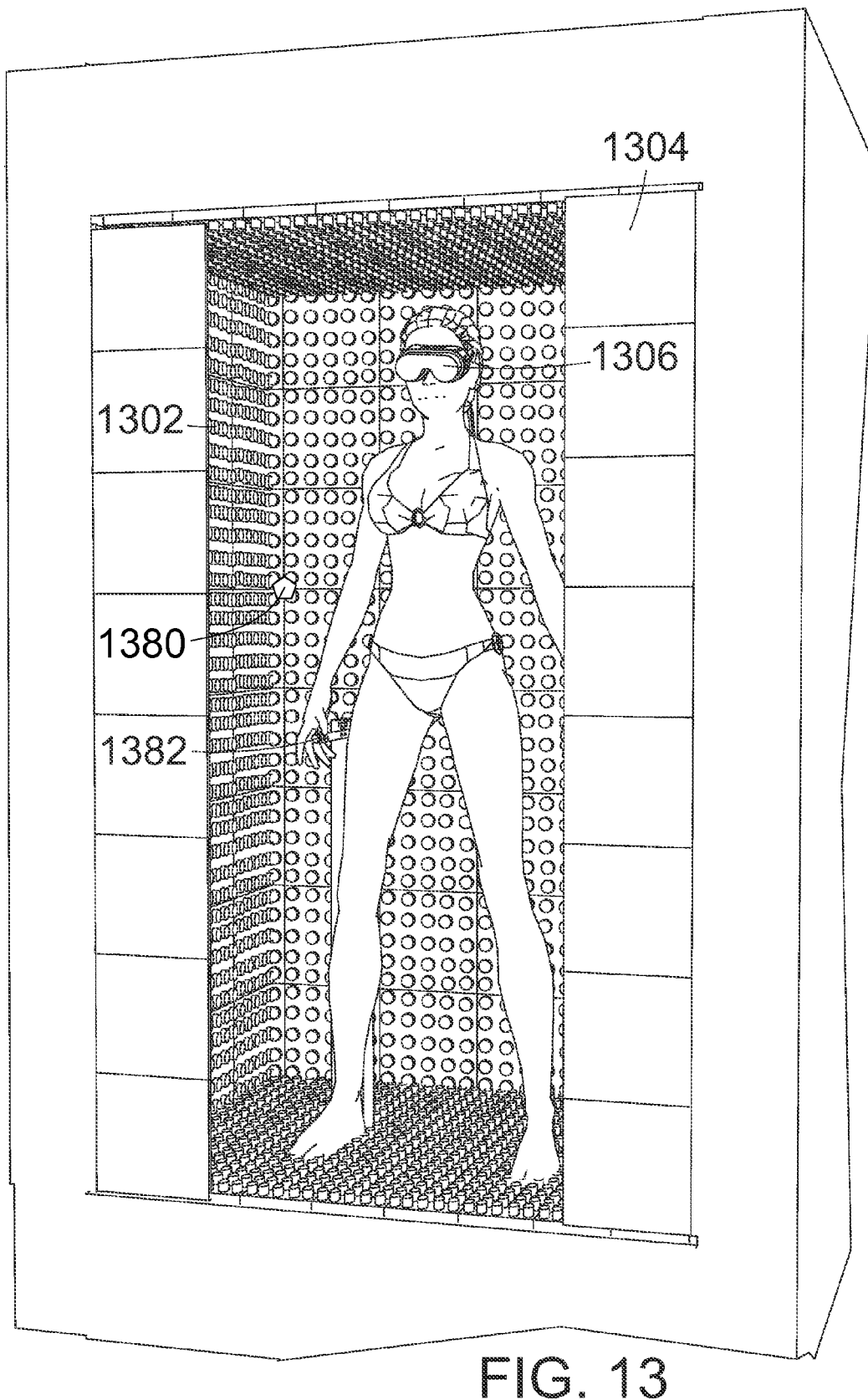
FIG. 13 shows a perspective view of a stationary cameras, and 3D imaging lasers attached to an inside of enclosed walls of a semi-cube surrounding a user holding rail, a joy stick attached to the rail, and 3D headset display.

An area for a user to stand in, is located next to walls of cameras 1302, as shown in FIG. 13. A computer (not shown) is connected to the cameras. The cameras 1302 are connected to camera tilting devices. Body imaging lasers 1380 are connected to the computer.

A three dimensional 3D HoloLens headset 1306, made by the Microsoft company, is connected to a computer. The headset could also be an Oculus Rift virtual reality headset, made by the Occults Rift Company. A thought controlling headset (not shown) made by the Emotiv Company, is connected to the computer. A body rail 1382 is connected to the imaging device.

A cluster of body contact health sensors similar to the contact health sensors used to contact the user's feet. The contact health sensor are located within a viewable outline that the user puts their feet on. The user's steps on the health sensors, when in the camera viewing area. Body imaging lasers are connected to the computer. The body viewing area is in semi-cube of cameras 1304.

Standing Full Body Scan by Stationary Cameras. Operation

The standing user sees the images of their body taken by the cameras, in the Hololens headset 3D display, as shown in FIG. 13. The user can use their thoughts, eye tracking, midair hand gestures, or voice commands to change the view of their body that is being shown in on the display. The user uses the Emotiv thought device, to input their thoughts into the computer. The thoughts control or direct the view of the display. The though input can control a menu shown on the display, which can control the camera, etc.

The cameras 1302 on the floor of the device, compress into the floor when walked on. The compressed cameras image the sole or bottom of the user's feet that are on top of the camera. The user can steady and support their body by holding on the body rail 1382. The floor is clear, allowing the cameras to view the user's bottom of their feet.

The user stands in an area with in view of the cameras. The cameras images the user's body. The user views their body on the display. The user can zoom the camera's view in and out. The body imaging lasers 1380 fluoresce the user's body, allowing the cameras to create a 3D images of the user's body.

The cameras and their lens can tilt in the direction, of the area that the user wants to view on the tablet display. The tilting allows a more direct or perpendicular view of the viewed area. Increasing the direct view of the camera lens, increase the clarity of the view, and lessens distortion of the view if the cameras view was stationary. The stationary cameras view may be off center to a viewed area. The computer directs the lens tilting motors to move the tilt of the lens to an optimal viewing tilt. The cameras view can also be kept in a stationary position.

The user can view their body and look for possible health concerns. The less clothes on the body, the more of the user's body can be viewed, such as, the user being nude, or in a two piece bathing suit may allow more skin viewing area to be viewed.

The user stands in the viewing area, and holds on to a support pole. The tilting stationary cameras view the user. The user is viewed by the moving cameras. The user is scanned by the 3D imaging lasers. The s cameras view, and the 3D view is shown on the display, and viewed by the user. The different cameras views are stitched tighter, and shown in a window on the display. The 3D view is shown in its own window.

The computer analyses the views of the user, for possible skin cancer or other health ailments. If health ailments are detected, the detected aliment data is shown on the display. Health data that is normal or regular is shown on the display, such as, body temperature, blood sugar, blood pressure, body weight, heart rate, body fat percentage, etc.

Standing Body Scan by Health Sensors, and Camera Description

Figure 14:
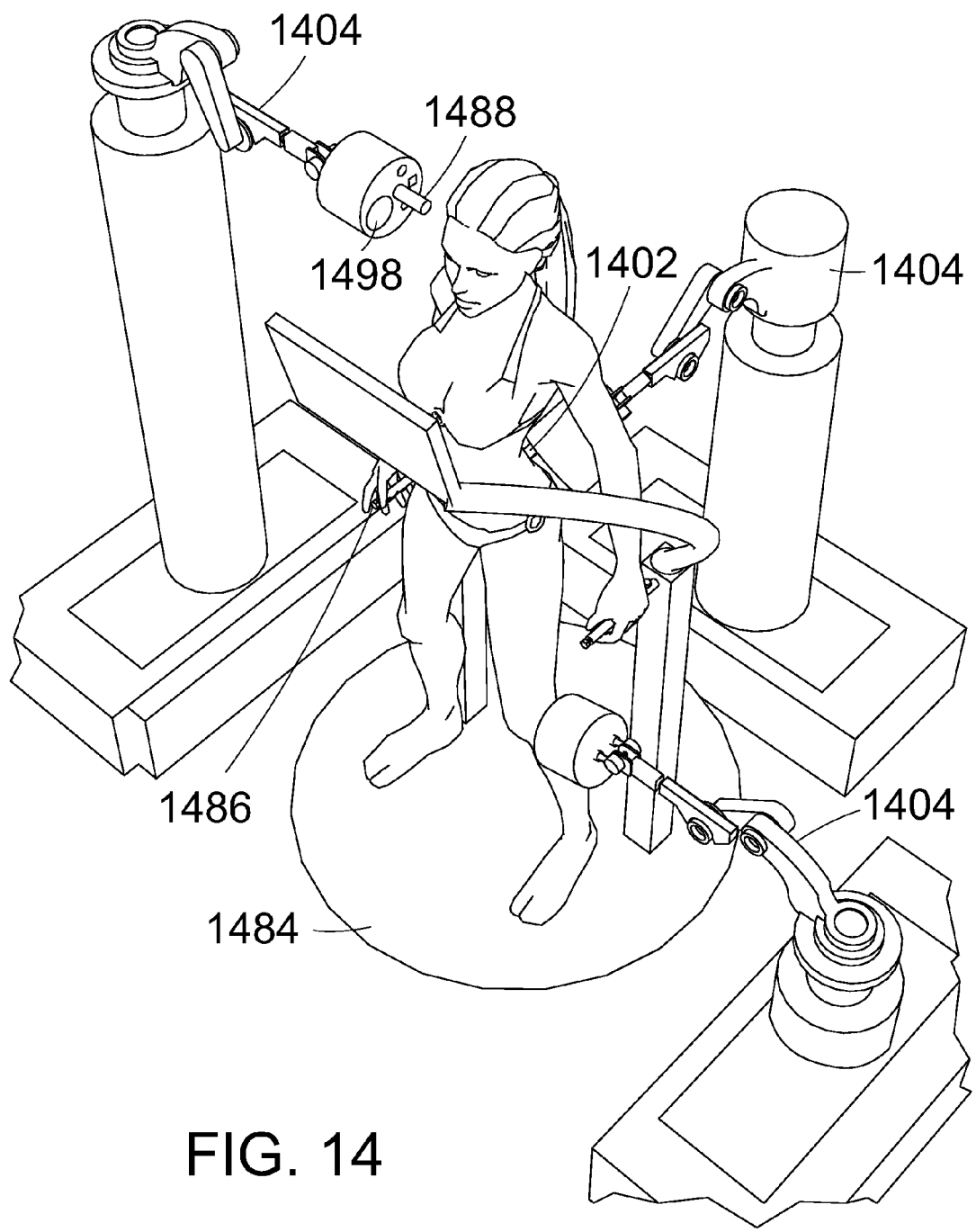
FIG. 14 shows a perspective view of a three camera moving devices, with cameras and heath sensors, adjacent to a rotational floor area, with a user holding rail, a joystick attached to the rail, and a computer attached to rail.

A breathing tube 1488 is attached to the camera device, as shown in FIG. 14. A breath malaria detector, developed by the Commonwealth Scientific and Industrial Research Organisation (CSIRO), of Australia is attached to the inside the tube. A lung cancer breath sensor made by Metabolomx, of California, or the University of Latvia is attached to inside the tube 1488, and connected to the computer. A stomach cancer breath sensor made by researchers in Israel is attached to inside the tube 1488, and connected to the computer.

A breath diabetes sensor developed by researcher in Massachusetts, is attached to inside the tube 1488, and connected to the computer. A Heart failure breath sensor made by Cleveland Clinic researchers is attached to inside the tube 1488, and connected to the computer. Kidney failure breath sensor made researchers is attached to inside the tube 1488, and connected to the computer. A breath tuberculous TB sensor is attached to inside the tube 1488, and connected to the computer.

An ultra sound sensor 1498 made by Royal Philips company, is connected to the computer. A rotating user platform 1484 is connected to the computer.

Standing Body Scan by Health Sensors, and Camera Operation

The breath malaria detector receives the breath of the user when the user blows into the breath tube 1488, and diagnoses malaria by detecting distinctive sulfur-containing chemical compounds in a patient's breath, as shown in FIG. 14. The malaria detector tests the breath for malaria. The breath is tested for diabetes, also a fruity breath odor, or an odor similar to acetone can point to a serious complication in diabetic patients called ketoacidosis. The tuberculous TB sensor searches for the breath signs of TB.

The breath is tested for lung and stomach cancer, using gas chromatography-mass spectrometry (GCMS). The breath is tested for kidney failure, which may be indicated by a mouth that smells fishy, urine-like, or similar to ammonia. Signs of heart failure are breath tested using mass spectrometry technology to analyze the breath samples for molecular and chemical compounds.

Ultrasound Sensor

This ultrasound sensor 1498 test uses sound waves to create images of the body and the internal organs. The camera moving device contacts the ultrasound sensor to the user's body. The sensor can be stationary on the body, or slowly moved on the body. Contact with the body maybe in areas, such as, the heart, arteries, and womb, etc. The sensor internally views the internal area, to easily and confidently assess disease states, and determine treatment. The ultrasound can be used for echo cardiograms, and for imaging the contents of the womb during pregnancy. The sensor is an Anatomically Intelligent Ultrasound (AIUS) tool that brings advanced quantification, automated 3D views and robust reproducibility to cardiac ultrasound imaging. An ultra sound gel may be used on the sensor during contact with the body to convey and receive acoustic energy (sound waves) to the body. The sensor extends and retracts into the moving device.

The user operates the joystick 1486 with contact from their fingers. The joystick controls the display's view of their body, and displayed menu, as shown in FIG. 14.

The platform 1484 the user stands on rotates, to let the camera and health sensors scan the whole body. The user stands on the body moving base, the base spins slowly to the left or right. The user or computer controls the rotation of the base. The user's body facing the cameras, is fully scanned as the users body moves in relationship to the cameras.

Figure 15:
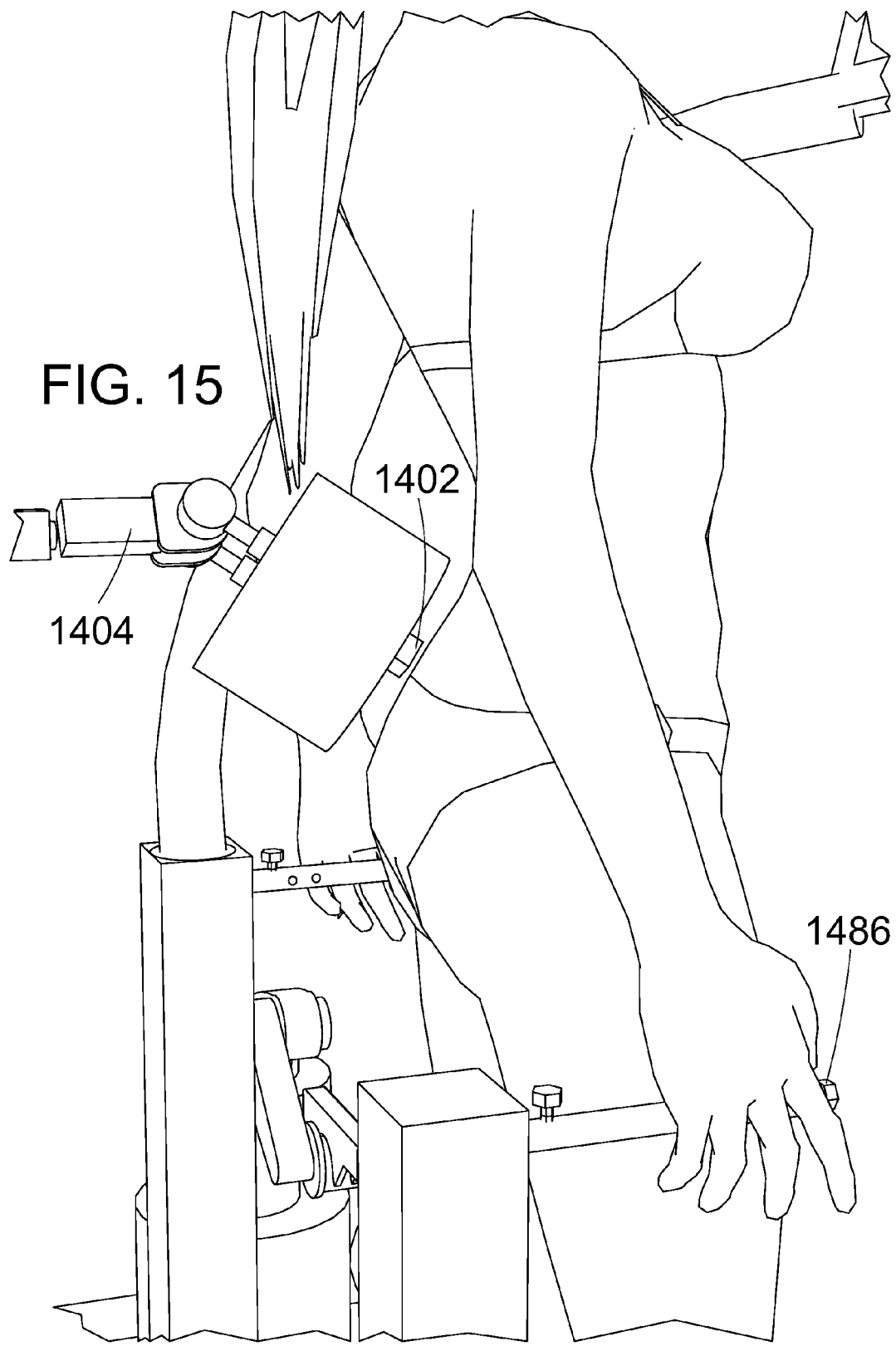
FIG. 15 shows a close up perspective view of camera incorporated into a camera moving device, and a joystick connected to a user holding rail.

The camera 1402 body health sensors are used to view and detect the health of user's body. The three camera moving devices 1404 move the camera and health sensors over the body. For safety the scanner turns off, if they contact the user's body inadvertently. The moving device moves the camera's view of the body as it moves over the body. The moving device keeps the cameras view to the user's perpendicular body as it move over the user's body, as shown in FIG. 15.

A User or Computer Directing a Bidet Water Stream Description

Figure 16:
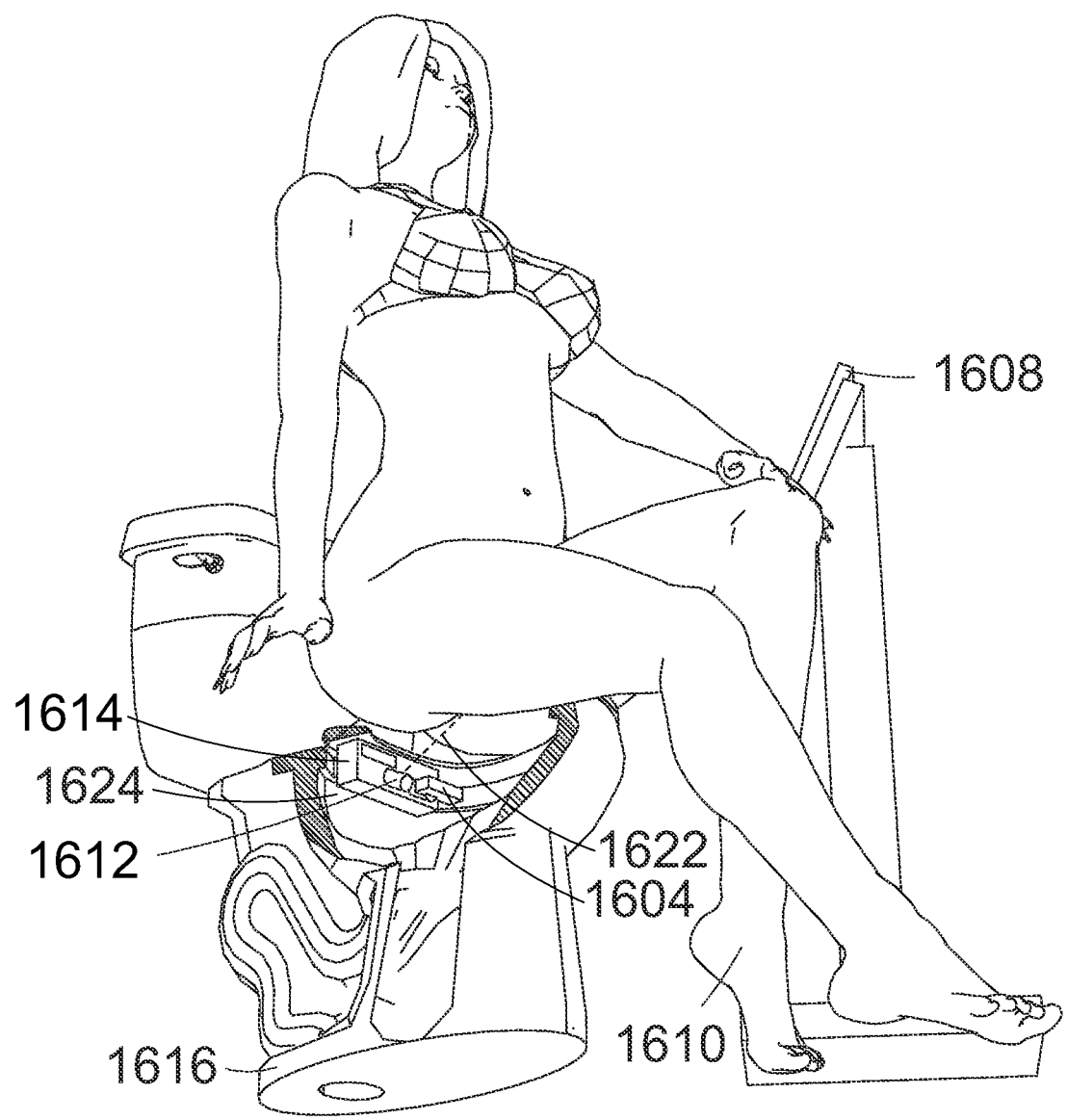
FIG. 16 shows a perspective view of a camera, and a computer or user bidet water aiming device inside a toilet, and a tablet computer.
Figure 17:
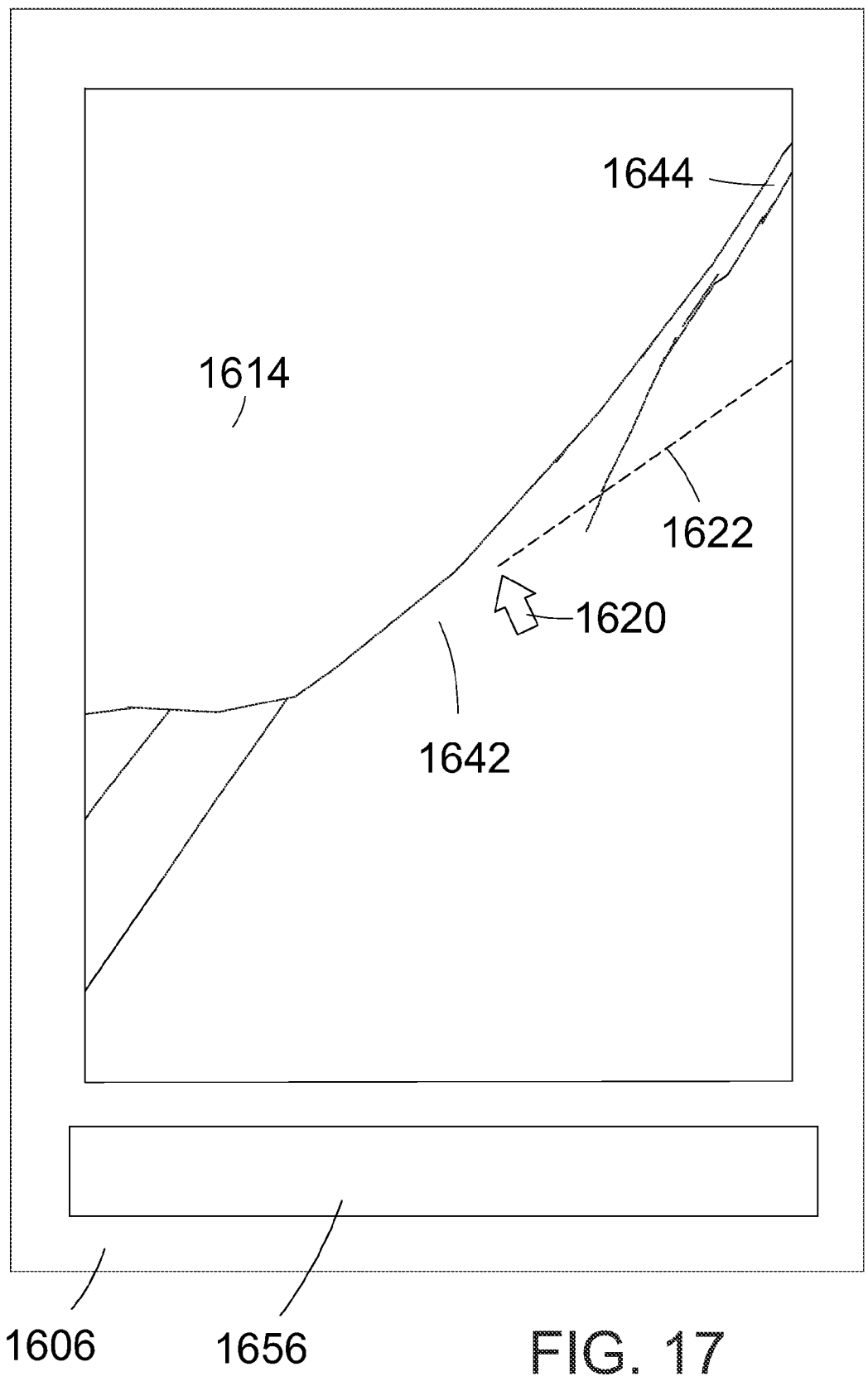
FIG. 17 shows a front view of a tablet computer, a mid-air hand gesture recognition sensor attached to the computer, a display, and the display shows a water stream contacting a user's posterior, and elimination positions.
Figure 18:
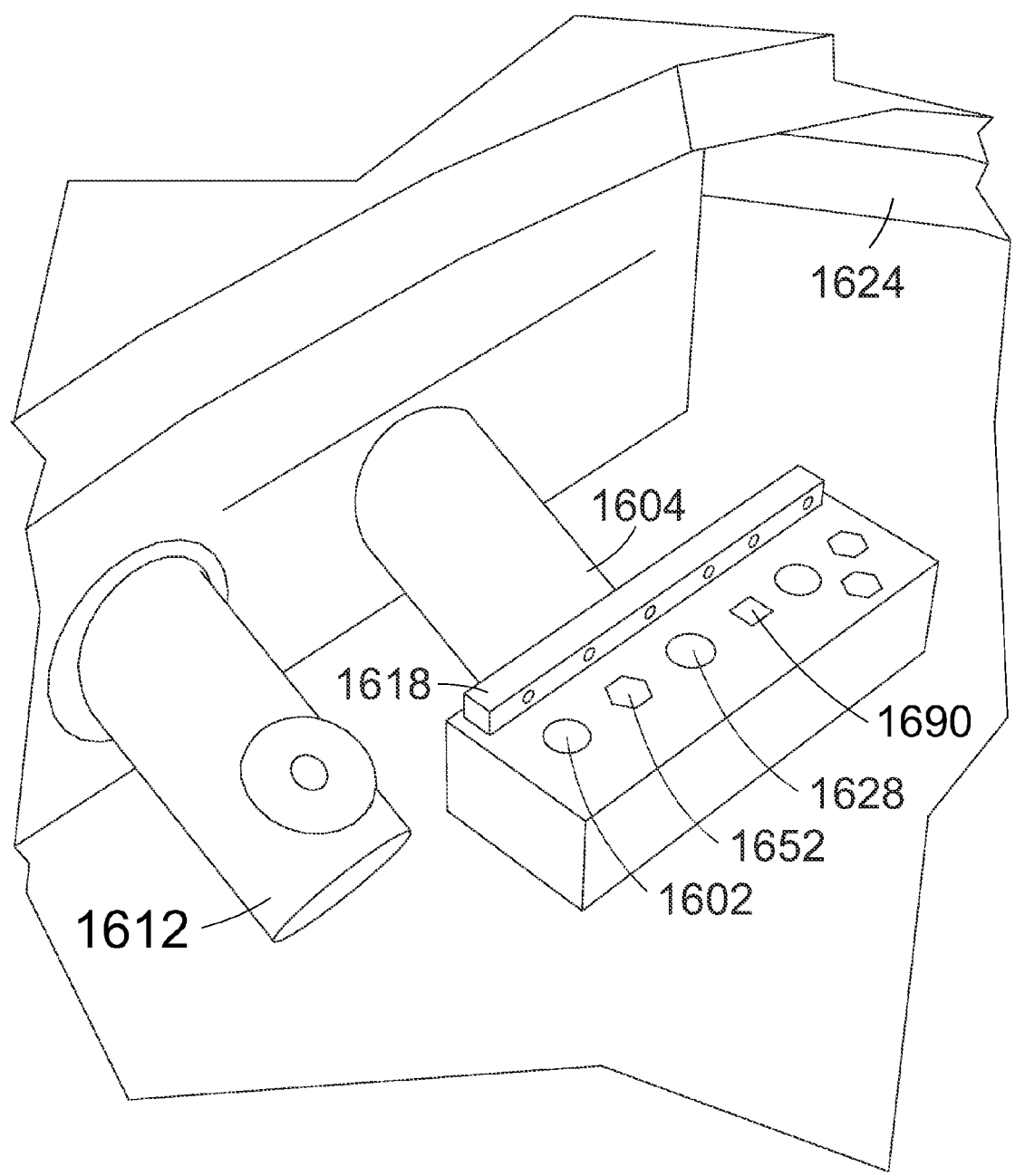
FIG. 18 shows a perspective view of a bidet water nozzle, and camera moving device connected to a bidet inside a toilet bowel, the camera moving device is attached to a camera, a ultrasonic distance sensor, a light, and health sensors.

A video camera 1602 is attached to one of two bidet wands. The camera is connected to a computer (not shown), as illustrated in FIGS. 16, 17, and 18. The camera 1602 is waterproofed. The camera lens is positioned in the wand with a view of the user's posterior. The second wand 1602 has a water nozzle. The wands are connected to a bidet 1614. The bidet is located inside a toilet bowel 1624. The bidet is connected to the computer. A display 1608 is connected to the computer. A user Leap 3D midair hand gesture recognition input device 1656, is made by the Leap Company, and is connected to the computer. The computer comprises a processor, the processor is programmed with a system operating software. The processor is connected to a memory for storing and retrieving data.

The camera moving wand 1604 has the camera 1602, an ultrasonic distance sensor 1652, a camera lens and distance sensor cleaning air nozzle 1618, bottom air dryer nozzle 1696, and a light 1628. The ultrasonic distance sensor 1652 is connected to the computer. The light is connected to the computer.

In an alternate embodiment the bidet wand components could be attached to one bidet wand. The one wand could have the water stream nozzle, and the camera, the ultrasonic distance sensor, the light, the air lenses, and the air body dryer nozzle.

The computer is programmed with ultrasonic distance measuring software, genital recognition software, fecal or blood recognition software, automatic bidet operating software, Leap mid-air hand gesture recognition software, and system operating software, etc.

A User Directed Bidet a Water Stream or Air Stream, Operation

The bidet water wand 1612 is used to stream water 1622 to the user's front 1642 and back elimination 1640 positions, as illustrated in FIGS. 16, 17, and 18. A user can move the bidet water stream, over their front and back elimination positions, and view the water contacting the elimination position, on the on the display 1608. The assembled bidet components, allow the user to visually direct, the water stream, to their elimination position while they are sitting on a toilet seat on a toilet 1616.

The user can view fecal matter on their back elimination position. A female user can view blood in the front elimination position. The water stream can be directed to the fecal matter or blood until there is visual confirmation that they have been washed off. After the washing the positions can be checked for any remaining fecal matter or blood, and if found the position can be rewashed.

When the user sits on the toilet seat, the light 1628 activates and illuminates the user's elimination positions. After eliminating the user can move the bidet water over their front and back elimination position, and view the water contacting the elimination position on the on the display.

The camera 1602 views where the water stream 1622 contacts the user. The view of the water stream, allows the user to visually direct the water stream to locations on their elimination position while they are sitting on the toilet seat. The camera views the positions before, during and after washing. The view are sent to the computer. The computer sends the images to the display. The display shows the video images of the user. An air stream is continually streamed over the lens to remove water that may fall on the lens. The ultrasonic distance sensor, allows the computer to measure the camera wands distance from the user, to maintain an optimal distance from the user. The computer visually senses the degradation of the camera's image, and turns off the air stream and activates the water stream.

The midair hand gesture input device is used to move the bidet wands. The user operates the bidet, by inputting using the Intel 3D midair input device 1656. The user uses the user's fingers movements in mid-air, to operate the mid-air input device. The midair input device's directs the movement of the wands and camera, etc. The user input midair device controls a cursor 1620 on the display screen 342. The user's finger movements move the cursor. The camera follows the movement of the cursor. The water stream 1622 streams the water, to where the cursor 1620 is located, on the shown body on the display.

The camera and water stream can move in unison. The camera views where the water stream contacts the user, and follows the stream, as the stream's contact moves on the user's elimination positions, and around the positions.

Bottom Air Dryer

The user directed air blower 1696 in the wand, allows the user to blow air on the user's elimination position. A second air blower (not shown) at the back of the toilet bowel 1624, can also dry the user's bottom, simultaneously while the user directs the air stream at the user's elimination position. The input device is used to direct the flow of air to desired positions on the user's posterior, and view the directing of air, on the display. The air removes water from the user's elimination positions Automatic Computer Streaming of Water to the Elimination Positions Operation The user requests, by inputting into the computer that either their front or back elimination positions be washed. The computer moves the camera, and water nozzle, to the requested elimination position. The position is either a default front or back elimination portion. After arriving at the default elimination position, the computer visually searches for the associated elimination position, such as, searching for female genitalia.

The computer identifies the female elimination position, and location. The computer automatically identifies the user's elimination positions and streams water to the elimination positions location. The computer visually aims the water stream at the elimination position. The aiming of the stream of the water, by the computer assures that the water stream is accurately delivered to the elimination position, when the elimination position may be positioned at different locations at different times, or if the user moves while being washed.

The computer can move to either a female and or male back elimination position, or a female's front elimination position. The male can request to have their front elimination position washed. A clock shown on the display countdowns down, showing the duration of the water wash cycle, starting at 20 seconds. The water stream will follow the user's elimination position if the user move while water is being streamed to the elimination position.

The bidet's water stream moves to the user's elimination positions, instead of the user having to move the position to the bidet water stream. If the user is sitting off center on the toilet seat, the wand will move the water stream, to the users off center elimination positions. The water stream will adjust its position, to target the elimination positions. Different locations of elimination positions maybe due to, people having different shapes and sizes.

The computer can view and identify fecal matter on their back elimination position, by using the fecal or blood recognition software. A female user can view blood in the front elimination position. The water stream can be directed to the fecal matter or blood until there is visual confirmation that they have been washed off. After washing the positions can be checked for any remaining fecal matter or blood, and if found the position can be rewashed.

After the user's elimination position is washed, the computer directs a stream of air from the wand, at the user's elimination position to dry and remove water from the position. The computer identifies the washed user elimination position, by remembering the position that was just washed. Air is streamed out of the air nozzle 1696 in the bidet wand, as illustrated in FIG. 18.

The clock displays a countdown, showing the duration of the air drying cycle, starting at 25 seconds. The elimination position dryer finishes when the clock counts down to 0 seconds. The bidet's air stream moves to the user's bottom cleaning positions without the user having to move to the air stream.

Software Flowcart

Figure 25:
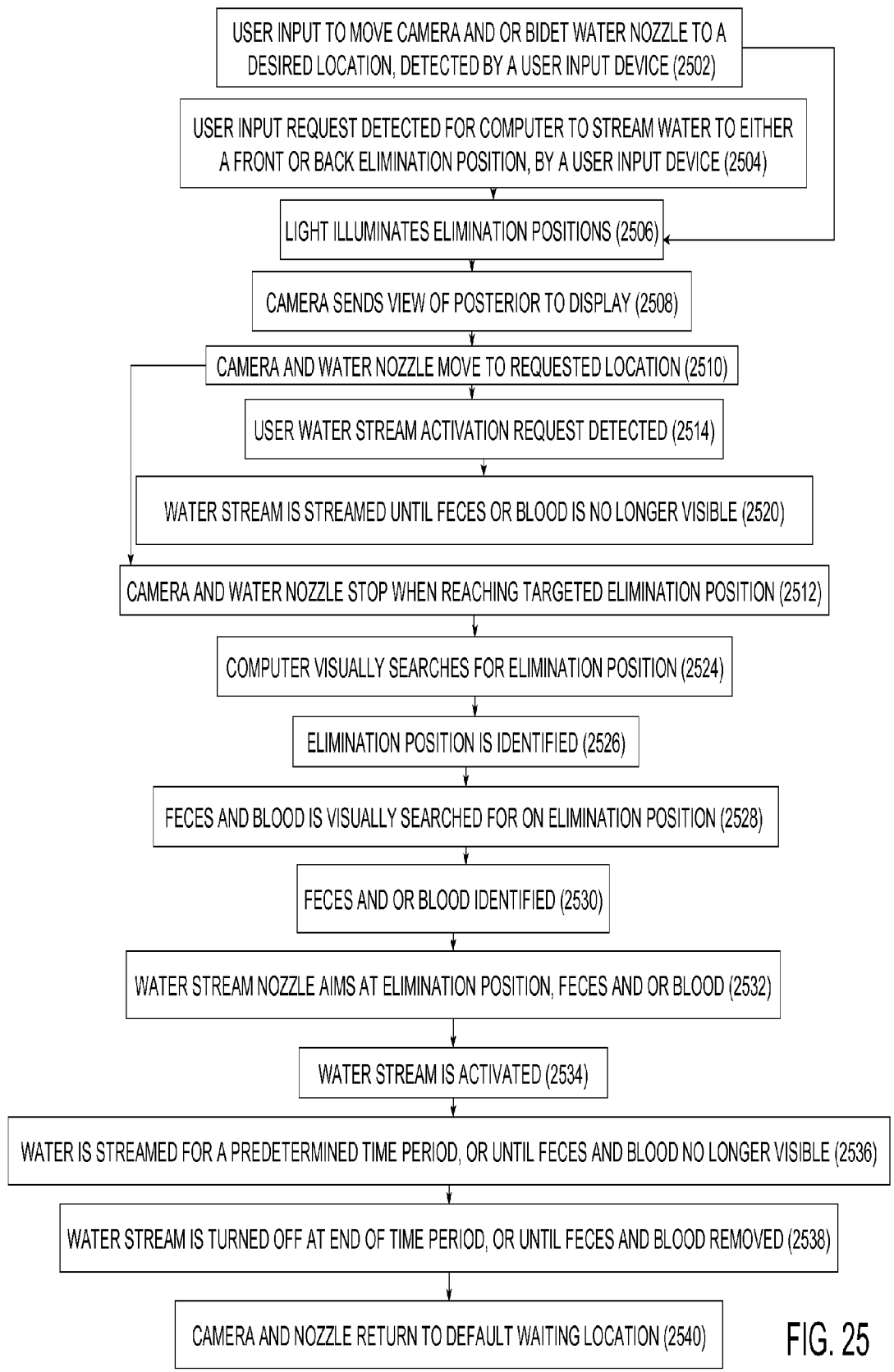
FIG. 25 depicts a software flowchart of a user or computer operated visual bidet water streaming device.

FIG. 25 shows software steps of the operation of the user or computer directed bidet water stream, user input to move camera and or bidet water nozzle to a desired location, detected by a user input device (2502), user input request detected for computer to stream water to either a front or back elimination position, by a user input device (2504), light illuminates elimination positions (2506), camera sends view of posterior to display (2508), camera and water nozzle move to requested location (2510), user water stream activation request detected (2514), water stream is streamed until feces or blood is no longer visible (2520), camera and water nozzle stop when reaching targeted elimination position (2512), computer visually searches for elimination position (2524), elimination position is identified (2526), feces and blood is visually searched for on elimination position (2528), feces and or blood identified (2530), water stream nozzle aims at elimination position, feces and or blood (2532), water stream is activated (2534), water is streamed for a predetermined time period, or until feces and blood no longer visible (2536), water stream is turned off at end of time period, or until feces and blood removed (2538), camera and nozzle return to default waiting location (2540).

Block Diagram

Figure 24:
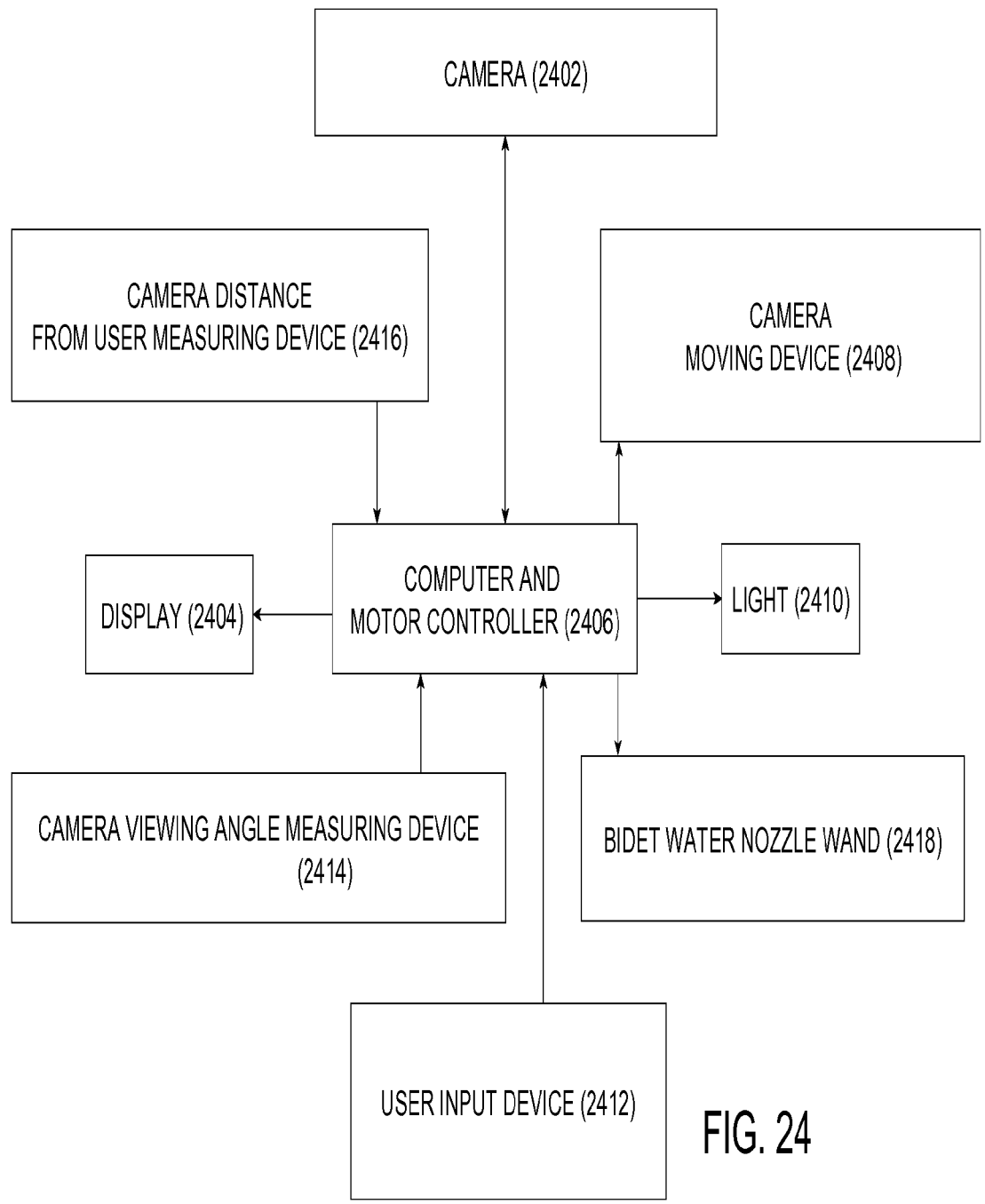
FIG. 24 illustrates a block diagram of hardware connections between components of a user or computer operated visual bidet water streaming device.

FIG. 24, illustrates a block diagram of some of the hardware components connections of the device, camera (2402), display (2404), computer and motor controller (2406), camera moving device (2408), light (2410), user input device (2412), camera viewing angle measuring device (2414), camera distance from user measuring device (2416), BIDET WATER NOZZLE WAND (2418).

Figure 6:
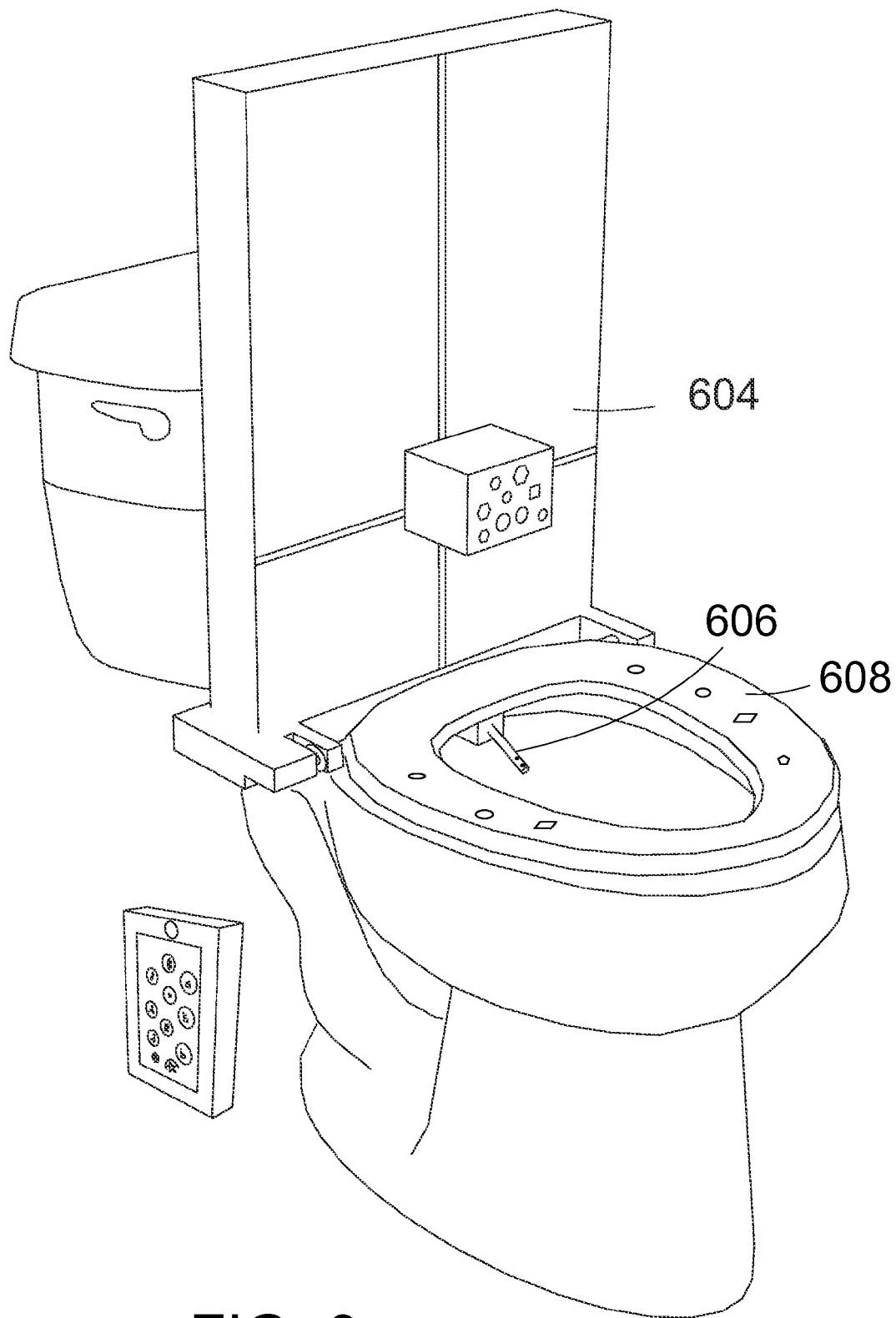
FIG. 6 shows a perspective view of a back camera and health sensor moving, a health sensing toilet seat, and a computer operated bidet, and tablet computer.

Three Embodiments Combined, a Body Viewing Camera, Health Sensors and Health Cameras, and a Visually Directed Bidet Water Stream Description and Operation Three embodiments can be combined into one embodiment, such as, a user can view a cameras view of their body on the display, they can sense or measure their health with the camera and health sensors, and they or a computer can direct a bidet water stream on their elimination positions, as illustrated in FIG. 6.

The three embodiments are described and listed. 1. The body viewing camera 604 is helpful in allowing the user to view, on a display, areas of their body that are difficult to view, such as, the back, and posterior. The camera can also be moved to view the entire body.

2. Health sensors, and cameras attached to a toilet seat 608 measure and diagnose the health conditions of the user body, such as, blood pressure, blood glucose, or skin cancer, etc. Depending on the health sensors, and cameras the sensors, and cameras can either view or contact areas of the user's body. The health results are shown on a display viewable by the user.

3. The bidet water stream is directed at the user's elimination positions, visually by a user, or a computer. A camera connected to a bidet wand 606, views the bidets water stream's contact on the user's elimination positions. The user or computer can use the view of the water stream, to move the water stream to desired areas on the elimination positions. The visual directing of the water stream allows a more accurate directing of the water stream on the user's elimination positions. Fecal matter can be automatically visually identified and washed off by the computer. The user can visually view their elimination positions to be sure that they have been thoroughly washed.

CONCLUSIONS, RAMIFICATIONS AND SCOPE

Conclusion

From the preceding description and drawings it becomes apparent that the user, may use the user health camera to manually or automatically visually inspect difficult to view areas of their body, such as, their posterior, and back. The heath sensors may preform health test on the user's body. Health information may help a user become more aware of their body. The user or computer can visually direct a bidets water stream to their elimination positions.

The camera moving device can be used to scratch an itch on the user's body. Minor surgery could be performed on the body's surface, such as, the removal of warts, etc.

Thus the reader will see that at least one embodiment, of the user health camera, and health sensors, provides a more reliable, healthier and economical device that can be used by persons of almost any age. It will be apparent that various changes and modifications can be made, without departing from the scope of the various embodiments, as defined in the claims.

Thus the scope of the embodiments, should be determined by the appended claims, and their legal equivalents, rather than by the examples given.

I claim:

1. A method for viewing a user's body comprising,
    viewing a user's body with one or more cameras connected to a computer, wherein the one or more cameras are positioned to view the user's body, wherein the view of the user's body is sent to the computer;
    showing the view of the user's body with a display connected to the computer, wherein the view of the user's body is sent to the display by the computer,
    positioning a plurality of the one or more cameras on a bottom of a toilet seat lid of a toilet to view the user's back while the user is sitting on the toilet,
    detecting a skin cancer from the view of the user's back with a cancer detecting software in the computer,
    displaying a detection of the skin cancer on the display with a detection display software in the computer.

2. The method of claim 1, further comprising the step of: providing skin cancer illuminating LED lights on the bottom of the toilet seat lid.

3. The method of claim 1, further comprising the step of: expanding the toilet set lid vertically to allow the plurality of the one or more cameras to completely view the user's back.

4. The method of claim 1, further comprising the step of: alerting the user to the detection of the skin cancer with a speaker.

5. The method of claim 1, further comprising the step of: communicating the detection of the skin cancer from the computer to healthcare providers via the internet.

6. The method of claim 1, further comprising the step of: displaying an image of the detected skin cancer on the display, wherein the image of the detected skin cancer is captured by the plurality of the one or more cameras.

* * * * *